US011253476B2

(12) United States Patent
Fukushima

(10) Patent No.: US 11,253,476 B2
(45) Date of Patent: Feb. 22, 2022

(54) VACCINE ADJUVANT FORMULATION

(71) Applicant: Sumitomo Dainippon Pharma Co., Ltd., Osaka (JP)

(72) Inventor: Akihisa Fukushima, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 16/498,260

(22) PCT Filed: Mar. 28, 2018

(86) PCT No.: PCT/JP2018/012637
§ 371 (c)(1),
(2) Date: Sep. 26, 2019

(87) PCT Pub. No.: WO2018/181420
PCT Pub. Date: Oct. 4, 2018

(65) Prior Publication Data
US 2020/0121600 A1    Apr. 23, 2020

(30) Foreign Application Priority Data
Mar. 29, 2017  (JP) ............................... JP2017066280

(51) Int. Cl.
*A61K 9/127*     (2006.01)
*A61K 47/69*    (2017.01)
*A61K 47/54*    (2017.01)
*A61K 31/505*   (2006.01)
*A61K 39/39*    (2006.01)
*A61K 47/24*    (2006.01)
*A61K 47/28*    (2006.01)
*A61K 45/06*    (2006.01)

(52) U.S. Cl.
CPC ............ *A61K 9/127* (2013.01); *A61K 31/505* (2013.01); *A61K 39/39* (2013.01); *A61K 47/24* (2013.01); *A61K 47/28* (2013.01); *A61K 47/54* (2017.08); *A61K 47/69* (2017.08); *A61K 45/06* (2013.01)

(58) Field of Classification Search
CPC ........ A61K 9/127; A61K 47/69; A61K 47/54; A61K 31/505; A61K 39/39; A61K 47/24; A61K 47/28; A61K 45/06; A61K 39/00; A61K 45/00; A61K 47/06; A61P 31/00; A61P 35/00; A61P 37/04
See application file for complete search history.

(56) References Cited

U.S. PATENT DOCUMENTS

| 10,632,192 | B2 * | 4/2020 | Kimura ................... A61P 37/04 |
| 2003/0105323 | A1 | 6/2003 | Fujita et al. |
| 2007/0104776 | A1 | 5/2007 | Ishii et al. |
| 2013/0267532 | A1 | 10/2013 | Tosaki et al. |
| 2018/0280499 | A1 | 10/2018 | Kimura et al. |

FOREIGN PATENT DOCUMENTS

| WO | WO 2009/067081 | 5/2009 |
| WO | WO 2010/133885 | 11/2010 |
| WO | WO 2012/0663 3 5 | 5/2012 |
| WO | WO 2012/066336 | 5/2012 |
| WO | WO 2012/067268 | 5/2012 |
| WO | WO 2012/067269 | 5/2012 |
| WO | WO 2013/172479 | 11/2013 |

OTHER PUBLICATIONS

Dorwald, F. Zaragoza. Side Reactions in Organic Synthesis: A Guide to Successful Synthesis Design, Weinheim: WILEY-VCH Verlag GmbH & Co. KGaA, 2005, Preface (Year: 2005).*
EP Extended European Search Report in European Appln. No. 18774978.3, dated Nov. 10, 2020, 6 pages.
Klauber et al., "Delivery of TLR7 agonist to monocytes and dendritic cells by DCIR targeted liposomes induces robust production of anti-cancer cytokines," Acta Biomaterialia, Apr. 2017, 53:367-377.
Abhyankar et al., "Nanoformulation of synergistic TLR ligands to enhance vaccination against Entamoeba histolytica," Vaccine, 2017, 35:916-922.
Desmaele et al., "Squalenoylation: A generic platform for nanoparticular drug delivery," Journal of Controlled Release, 2012, 161:609-618.
Fox, "Squalene Emulsions for Parenteral Vaccine and Drug Delivery," Molecules, 2009, 14:3286-3312.
O'Hagan et al., "The mechanism of action of MF59—An innately attractive adjuvant formulation," Vaccine, 2012, 30:4341-4348.
Ott et al., "The Adjuvant MF59: A 10-Year Perspective," Methods on Molecular Medicine, 2000, 42:211-228.
PCT International Preliminary Report on Patentability in International Appln. No. PCT/JP2018/012637, dated Oct. 10, 2019, 9 pages.
PCT International Search Report in International Appln. No. PCT/JP2018/012637, dated May 22, 2018, 3 pages.
Peine et al., "Liposomal resiquimod for the treatment of Leishmania donovani infection," Journal of Antimicrobial Chemotherapy, 2014, 69:168-175.
Steinhagen et al., "TLR-based immune adjuvants," Vaccine, 2011, 29:3341-3355 (available online Aug. 14, 2010).
Tomai et al., "Resiquimod and other immune response modifiers as vaccine adjuvants," Expert Rev. Vaccines, 2007, 6(5):835-847.

* cited by examiner

*Primary Examiner* — Snigdha Maewall
(74) *Attorney, Agent, or Firm* — Fish & Richardson P.C.

(57) ABSTRACT

The present invention provides a liposome useful as a vaccine adjuvant. More specifically, the present invention provides a liposome which comprises a lipid bilayer comprising dimyristoylphosphatidylcholine and egg phosphatidylglycerol and a conjugated compound in which a low-molecular weight compound enhancing the physiological activity of TLR7 is bound to squalene via a linker, said conjugated compound being encapsulated in the lipid bilayer.

15 Claims, 3 Drawing Sheets

[Fig. 1]
Particle Size Distribution
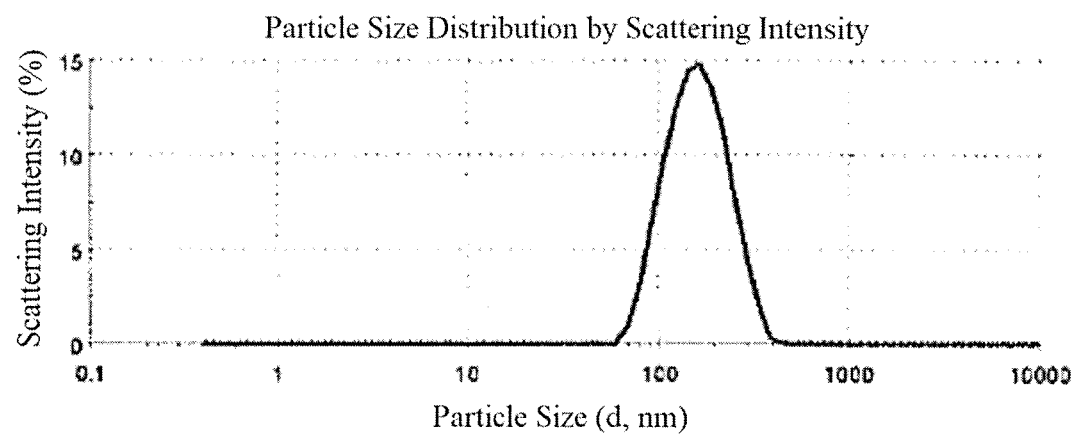
Zeta Electric Potential Distribution
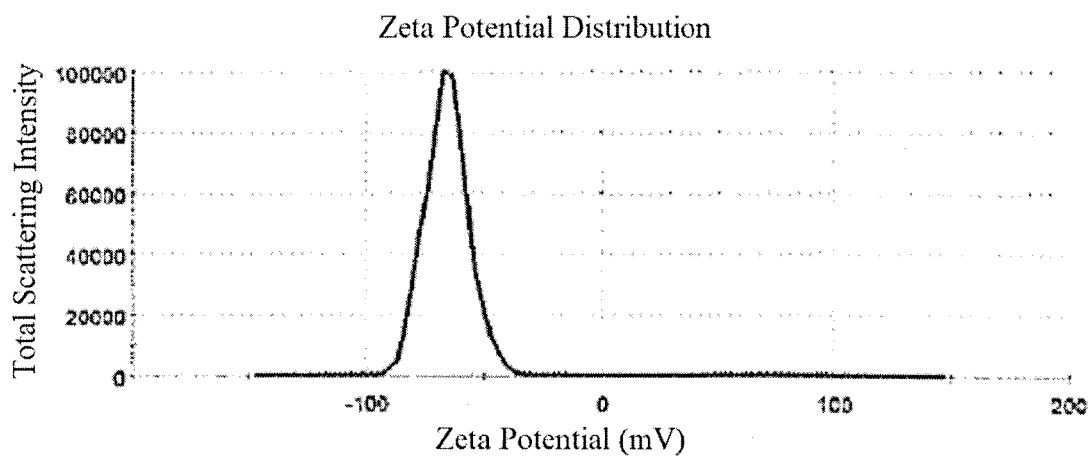

[Fig. 2]
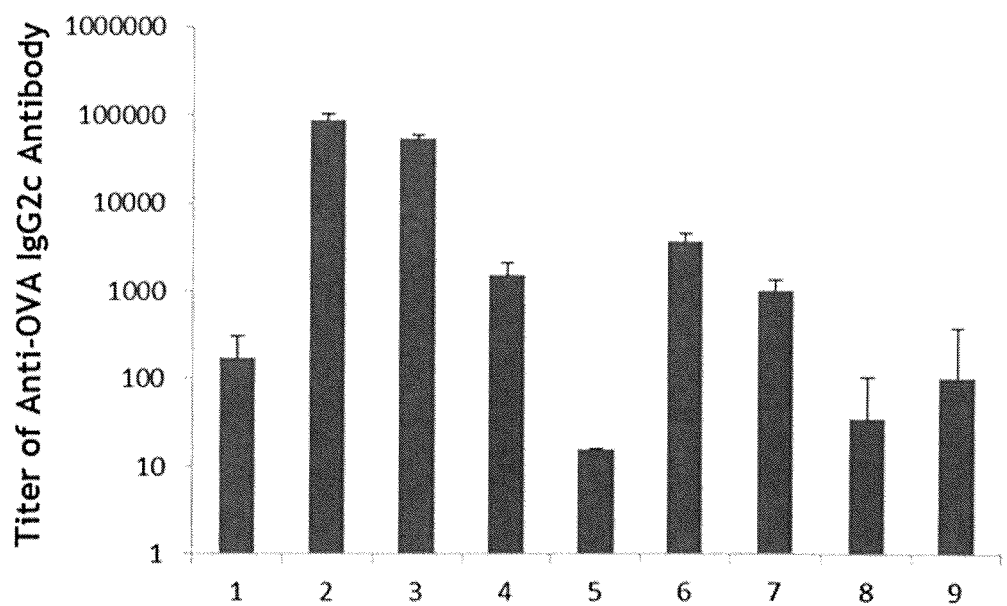
[Fig. 3]
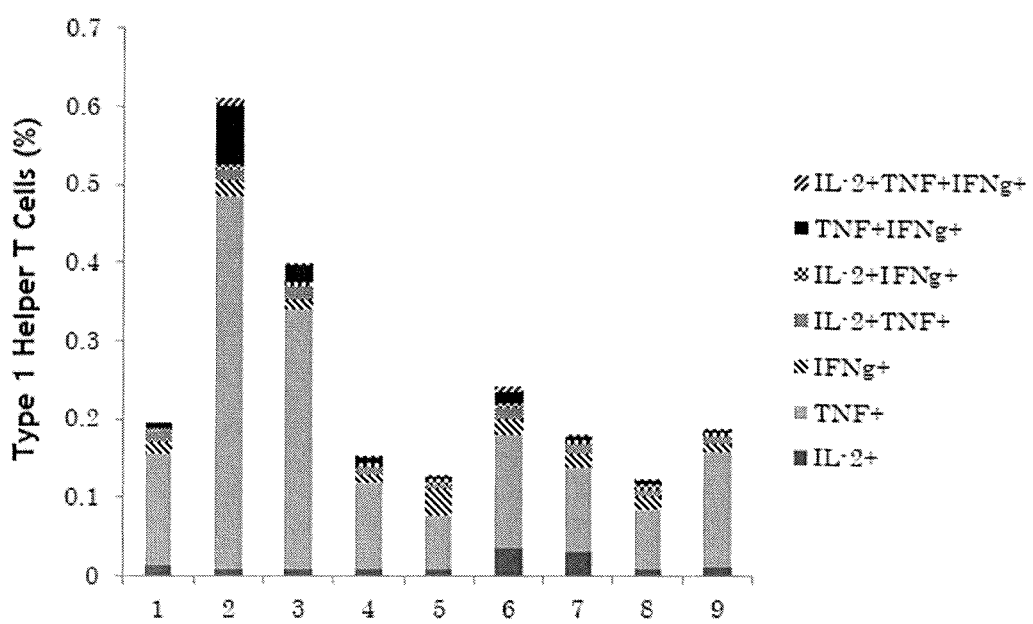

[Fig. 4]
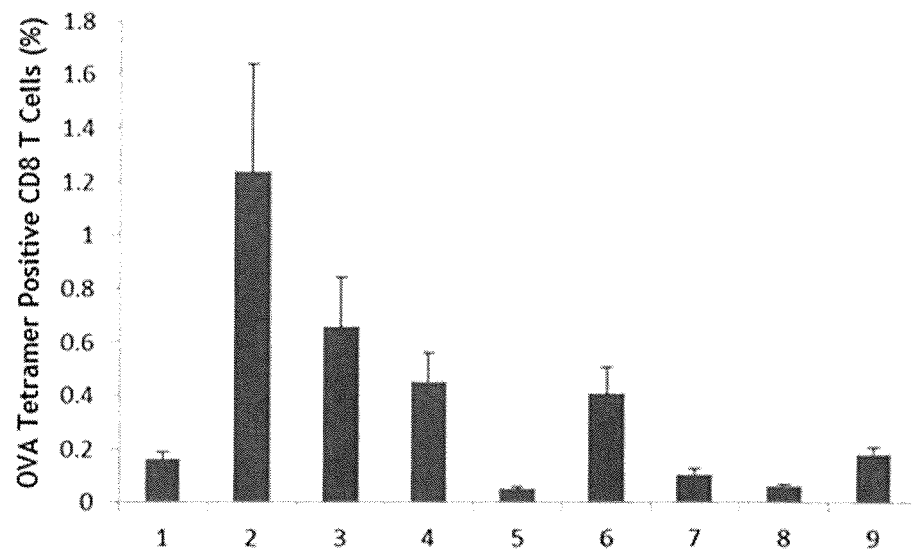
[Fig. 5]
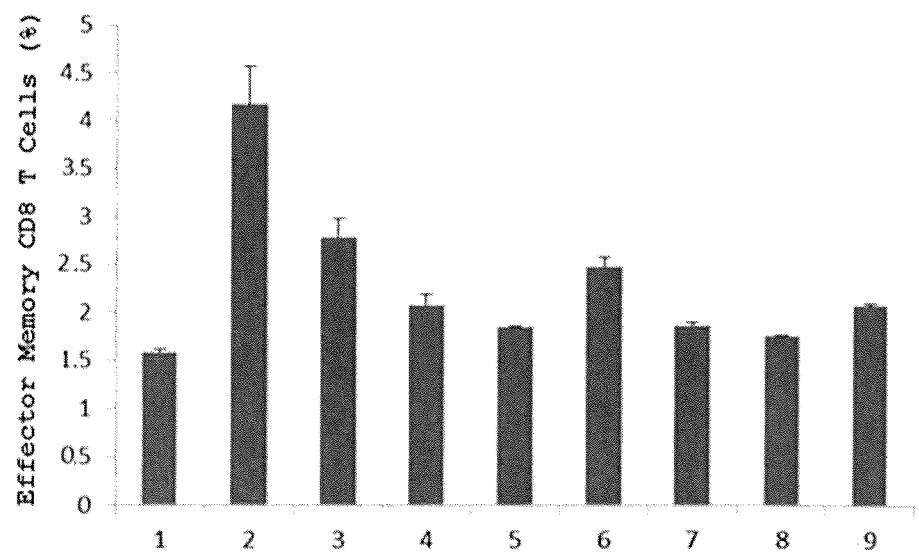

VACCINE ADJUVANT FORMULATION

TECHNICAL FIELD

The present invention relates to a liposome useful as a vaccine adjuvant, a composition comprising the liposome, and a use of the composition as a vaccine adjuvant.

BACKGROUND ART

Vaccines comprising a protein or a partial peptide thereof from microorganisms can be produced using chemical synthesis or genetic recombination technology and are advantageous in terms of safety and process for the production. On the other hand, subunit vaccines comprising a partial peptide (epitope) tend to have lower immuno-stimulating ability than that of live vaccines and inactivated vaccines. Accordingly, in order to enhance the immunogenicity of the epitope and to improve the immuno-stimulating activity of the vaccine, it has been investigated for prophylactic or therapeutic methods using an adjuvant and an antigen in combination.

Adjuvants are an additive to enhance humoral and/or cellular immune responses to antigens, and adjuvants such as Alum and saponin have been used as a vaccine adjuvant.

Recently, it was revealed that Toll-like Receptor (TLR) plays an important role in the activation of innate immunity, which is a defense mechanism in living organisms against microorganisms. Of the known ten TLRs identified in human, TLR7 is activated by its agonist to activate dendritic cells (DC) and the like. As a result, expression of T cell costimulatory molecules (CD80, CD86, CD40) is enhanced, and inflammatory cytokines including type I interferon (especially IFNα), TNFα, IL-6 or IL-12 are produced.

In addition to such activation of DC, TLR7 agonists were known to activate B cells and further stimulate NK cells and T cells to promote IFNγ production, and therefore, it is expected to have a vaccine adjuvant activity. Indeed, adjuvant activity of TLR7 agonists, such as Resiquimod and Imiquimod, has been reported (Non-Patent Document 1).

From the above, there is need for development of new vaccine adjuvant that activates TLR7.

On the other hand, squalene is an oily substance used as an oil component for oil-in-water and water-in-oil emulsion preparations, and a squalene-containing adjuvant such as MF59 has been used as an adjuvant for influenza vaccine (Non-Patent Documents 2, 3 and 4).

PRIOR ART

Patent Documents

[Patent Document 1] WO00/12487
[Patent Document 2] WO2009/067081
[Patent Document 3] WO2010/133885
[Patent Document 4] WO2012/066335
[Patent Document 5] WO2012/066336
[Patent Document 6] WO2012/067268
[Patent Document 7] WO2012/067269
[Patent Document 8] WO2013/172479

Non-Patent Documents

[Non-Patent Document 1] Steinhagen, F. et al., Vaccine, 14 Aug. 2010, Vol. 29, pp. 3341-3355
[Non-Patent Document 2] M. A. Tomai et al, Exp. Rev. Vaccine, 6, 835
[Non-Patent Document 3] G. Ott et al. Methods in Molecular Medicine, 2000, 42, 211-228
[Non-Patent Document 4] D. T. O'Hagan et al. Vaccine 2012, 4341-4348
[Non-Patent Document 5] C. B. Fox, molecules 2009, 14, 3286

SUMMARY OF INVENTION

Problem to be Solved by the Invention

The present invention provides a composition useful as a vaccine adjuvant which is excellent in long-term stability and immuno-stimulating activity.

Means to Solve the Problem

As a result of dedicated studies, the present inventors discovered that a compound wherein a low-molecular-weight compound, which is a TLR7 agonist that enhances the physiological activity (function) of Toll-like Receptor 7 (TLR7), is chemically bound to squalene via a spacer (hereinafter referred to as "a conjugated compound of the invention") exhibits excellent adjuvant activity by encapsulating in a liposome comprising a certain lipid component.

The present invention is as set forth below.

[1] A liposome comprising (1) and (2):
(1) a lipid multilayer comprising
a mixture of two different lipids selected from the group consisting of: hydrogenated soybean phosphatidylcholine (HSPC), dioleoylphosphatidylcholine (DOPC), distearoylphosphatidylglycerol (DSPG), dioleoylphosphatidylglycerol (DOPG), dimyristoylphosphatidylcholine (DMPC) and egg yolk phosphatidylglycerol (EPG), or
a mixture of the two different lipids and cholesterol (Chol); and
(2) a conjugated compound in which a low-molecular weight compound that enhances the physiological activity of TLR7 is chemically bound via a spacer to squalene or to a lipid derived from squalene, said conjugated compound being encapsulated in the lipid multilayer of (1).
[2] The liposome according to [1], wherein the weight ratio of the conjugated compound to the lipid components is 1:8 to 1:250.
[3] A liposome comprising the conjugated compound according to [1] or [2], wherein the lipid multilayer of (1) is a lipid multilayer comprising lipid components comprising a mixture of dimyristoylphosphatidylcholine (DMPC) and egg yolk phosphatidylglycerol (EPG).
[4] The liposome according to any one of [1] to [3], wherein the molar ratio of dimyristoylphosphatidylcholine (DMPC) to egg yolk phosphatidylglycerol (EPG) is 1:1 to 2:1.
[5] The liposome according to any one of [1] to [4] characterized in that the low-molecular-weight compound which enhances the physiological activity of TLR7 has a molecular weight of 200 to 600 and has an adenine skeleton, a pyrimidine skeleton, an imidazoquinoline skeleton, an imidazopyridine skeleton or a quinazoline skeleton.

[6] The liposome according to [5] wherein the low-molecular-weight compound which enhances the physiological activity of TLR7 has a pyrimidine skeleton, an adenine skeleton or an imidazoquinoline skeleton.

[7] The liposome according to [6] wherein the low-molecular-weight compound which enhances the physiological activity of TLR7 comprises a structure of the formula (2), said low-molecular-weight compound being bound to the spacer:

[Chem. 1]

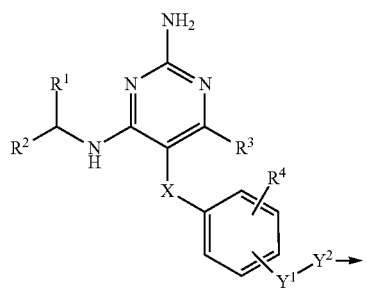

(2)

wherein

[Chem. 3]

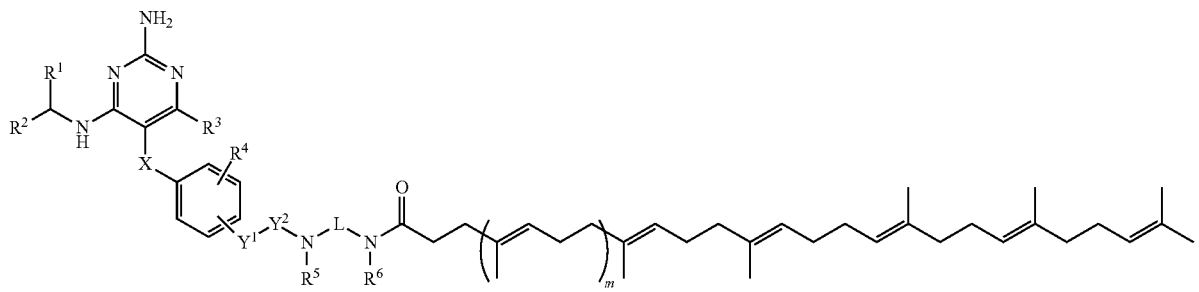

(1)

X is methylene, oxygen atom, sulfur atom, SO, $SO_2$ or $NR^7$ wherein $R^7$ is hydrogen atom or an alkyl group of 1 to 3 carbon atoms;

$R^1$ and $R^2$ are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group, halogen atom and an alkoxy group of 1 to 6 carbon atoms;

$R^3$ is an alkyl group of 1 to 6 carbon atoms, an alkoxy group of 1 to 6 carbon atoms or an alkylthio group of 1 to 6 carbon atoms;

$R^4$ is hydrogen atom, halogen atom, hydroxy group, an alkyl group of 1 to 6 carbon atoms, an alkoxy group of 1 to 6 carbon atoms or cyano group;

$Y^1$ is a single bond, $-(CR^9R^{10})_p-$, $-CH=CH-(CR^9R^{10})_q-$, $$-C\equiv C-(CR^9R^{10})_{q'}-$$ [Chem. 2]

or $-(CR^9R^{10})_r-O-(CR^{9'}R^{10'})_{r'}-$ wherein $R^9$, $R^{10}$, $R^{9'}$ and $R^{10'}$ are independently hydrogen atom or an alkyl group of 1 to 4 carbon atoms;

$Y^2$ is a single bond or $-C(O)-$;

provided that when the alkyl group is substituted, it is substituted with 1 to 4 same or different substituents selected from the group consisting of hydroxy group and halogen atom;

p is an integer of 1 to 6;

and q' are independently an integer of 0 to 4;

r is an integer of 0 to 5, and r' is an integer of 1 to 5, provided that the sum of r and r' is 5 or less and provided that r' is an integer of 2 or more when $Y^2$ is a single bond; and the arrowed line represents a bond to the spacer.

[8] The liposome according to any one of [1] to [6] wherein the conjugated compound is a compound of the formula (1) or a pharmaceutically acceptable salt thereof:

wherein

X is methylene, oxygen atom, sulfur atom, SO, $SO_2$ or $NR^7$ wherein $R^7$ is hydrogen atom or an alkyl group of 1 to 3 carbon atoms;

$R^1$ and $R^2$ are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group, halogen atom and an alkoxy group of 1 to 6 carbon atoms;

$R^3$ is an alkyl group of 1 to 6 carbon atoms, an alkoxy group of 1 to 6 carbon atoms or an alkylthio group of 1 to 6 carbon atoms;

$R^4$ is hydrogen atom, halogen atom, hydroxy group, an alkyl group of 1 to 6 carbon atoms, an alkoxy group of 1 to 6 carbon atoms or cyano group;

$Y^1$ is a single bond, $-(CR^9R^{10})_p-$, $-CH=CH-(CR^9R^{10})_q-$, $$-C\equiv C-(CR^9R^{10})_{q'}-$$ [Chem. 4]

or —(CR$^9$R$^{10}$)$_r$—O—(CR$^{9'}$R$^{10'}$)$_{r'}$— wherein R$^9$, R$^{10}$, R$^{9'}$ and R$^{10'}$ are independently hydrogen atom or an alkyl group of 1 to 4 carbon atoms;

Y$^2$ is a single bond or —C(O)—;

L is a substituted or unsubstituted straight chain alkylene of 2 to 6 carbon atoms or a divalent group derived from 4- to 8-membered cycloalkane, provided that when the straight chain alkylene or the cycloalkane is substituted, it is substituted with 1 to 4 same or different substituents selected from the group consisting of alkyl group of 1 to 5 carbon atoms, hydroxy group and halogen atom, and provided that any one of the methylene group in the straight chain alkylene of L is optionally replaced with carbonyl group;

R$^5$ and R$^6$ are independently hydrogen atom or a substituted or unsubstituted alkyl group of 1 to 6 carbon atoms, or either R$^5$ or R$^6$ is taken together with any carbon atom of L to form a 4- to 8-membered nitrogen-containing saturated heterocycle, or R$^5$ and R$^6$ are taken together to form a substituted or unsubstituted 5- to 8-membered nitrogen-containing saturated heterocycle, provided that when the alkyl group is substituted, it is substituted with 1 to 4 same or different substituents selected from the group consisting of hydroxy group and halogen atom and provided that when the 4- to 8-membered nitrogen-containing saturated heterocycle or the 5- to 8-membered nitrogen-containing saturated heterocycle is substituted, it is substituted with same or different 1 to 4 substituents selected from the group consisting of methyl group, ethyl group, propyl group, hydroxymethyl group, hydroxyethyl group, carbonyl group, hydroxy group and halogen atom;

m is 0 or 1;

p is an integer of 1 to 6;

q and q' are independently an integer of 0 to 4; and r is an integer of 0 to 5, and r' is an integer of 1 to 5, provided that the sum of r and r' is 5 or less and provided that r' is an integer of 2 or more when Y$^2$ is a single bond.

[9] The liposome according to any one of [1] to [8], wherein the lipid multilayer is a lipid bilayer.

[10] A pharmaceutical composition comprising the liposome according to any one of [1] to [9].

[11] A vaccine adjuvant comprising the liposome according to any one of [1] to [9].

[12] A vaccine comprising the liposome according to any one of [1] to [9] and an antigen.

[13] The vaccine according to [12] wherein the antigen is a substance derived from a pathogen.

Effect of the Invention

The vaccine adjuvant of the invention enables to enhance specific immune response to an antigen and is stable over a long period of time.

BRIEF DESCRIPTION OF DRAWINGS

FIG. 1 shows the results of particle size distribution and Zeta electric potential distribution of the liposome of Example 5, which was diluted with purified water immediately after the preparation thereof and measured by dynamic light scattering method using MALVERN Zetasizer Nano. The ordinate represents the scattering intensity, and the abscissa represents the particle size and the Zeta potential, respectively.

FIG. 2 shows the results of ELISA quantification of OVA-specific IgG2c in serum of immunized mice, which were intramuscularly administered with the liposomes of Example 1 and Example 5. The ordinate represents the antibody titer of OVA-specific IgG2c in serum. The abscissa represents administered samples, which are as follows (the doses of liposome or Alum as administered are indicated in the parentheses). 1: negative control of Example 5 (liposome containing no conjugated compound, i.e., empty liposome the lipid weight of which is equivalent to that administered with 50 μg/mouse of conjugated compound); 2: liposome of Example 5 (50 μg/mouse); 3: liposome of Example 5 (10 μg/mouse); 4: liposome of Example (2 μg/mouse); 5: negative control of Example 1 (liposome containing no conjugated compound, as in the above 1); 6: liposome of Example 1 (10 μg/mouse); 7: liposome of Example (2 μg/mouse); 8: liposome of Example 1 (0.4 μg/mouse); 9: Alum (Aluminum hydroxide) (150 μg/mouse).

FIG. 3 is a graph showing the proportion of type 1 helper T cells in spleen cells of mice, which were administered intramuscularly with the liposome of Example 1 or Example 5. The abscissa represents the same as in FIG. 2.

FIG. 4 is a graph showing the proportion of OVA tetramer positive CD8 T cells in spleen cells of mice, which were administered intramuscularly with the liposome of Example 1 or Example 5. The abscissa represents the same as in FIG. 2.

FIG. 5 is a graph showing the proportion of effector memory CD8 T cells in spleen cells of mice, which were administered intramuscularly with the liposome of Example 1 or Example 5. The abscissa represents the same as in FIG. 2.

DESCRIPTION OF EMBODIMENTS

Liposome is a microvesicle comprising a lipid multilayer, such as a bilayer membrane of amphiphilic lipid molecules (lipid bilayer), having an internal phase. Lipids that constitute such lipid multilayer may be herein referred to as lipid components. The lipid multilayer as used herein is preferably a lipid bilayer.

In the liposome that constitutes the formulation of the invention, the lipid components of the lipid multilayer, preferably the lipid bilayer, may comprise a mixture of two different lipids selected from the group consisting of: hydrogenated soybean phosphatidylcholine (HSPC: also referred to as hydrogenated soybean phospholipid), dioleoylphosphatidylcholine (DOPC), distearoylphosphatidylglycerol (DSPG), dioleoylphosphatidylglycerol (DOPG), dimyristoylphosphatidylcholine (DMPC) and egg yolk phosphatidylglycerol (EPG: also referred to as egg phosphatidylglycerol), or a mixture of such two different lipids and cholesterol (Chol).

If the lipid components constituting the liposome as mentioned above have an acidic group or a basic group, they may form a pharmaceutically acceptable salt such as an alkali metal salt (e.g., sodium salt, potassium salt).

The liposome of the invention may contain other components in an amount that does not affect substantially its stability.

In a certain embodiment, the lipid components that constitute a lipid bilayer comprise a mixture of DMPC and EPG. The molar ratio of DMPC to EPG (DMPC:EPG) is, for example, 1:10 to 10:1, preferably 1:4 to 4:1, more preferably 1:1 to 2:1.

In a particular embodiment, the molar ratio of DMPC to EPG (DMPC:EPG) is 5:3.

In a particular embodiment, the lipid components that constitute a lipid bilayer comprise a mixture of HSPC, Chol and DSPG. The proportion of each of HSPC, Chol and DSPG can be set appropriately between 10% and 60% to make 100% in total. For example, the ratio of HSPC:Chol:DSPG may be 50-60:25-30:10-25 (with the total of 100). In one example, HSPC:Chol:DSPG is about 53.1:about 26.3:about 20.5 (with the total of 100).

In a particular embodiment, the lipid components that constitute a lipid bilayer comprise a mixture of DOPC, Chol and DOPG. The propotion of each of DOPC, Chol and DOPG can be set appropriately between 10% and 60% to make 100% in total. For example, the ratio of DOPC:Chol:DOPG may be 50-60:25-30:10-25 (with the total of 100). In one example, DOPC:Chol:DOPG is about 53.1:about 26.3:about 20.5 (with the total of 100).

As used herein, "a conjugated compound being encapsulated in a lipid multilayer, preferably in a lipid bilayer" or "a conjugated compound encapsulated in a liposome" refers to a conjugated compound of the invention included inside a lipid multilayer, preferably a lipid bilayer, that constitutes the liposome, and also refers to a conjugated compound of the invention existing on the surface of or within a lipid multilayer, preferably a lipid bilayer, that constitutes the liposome.

The liposome of the invention can be obtained according to a known method for producing a liposome, using a conjugated compound and lipid components of the invention. For example, a predetermined amount of the conjugated compound of the invention and the lipid components are dissolved in a suitable organic solvent (chloroform, methanol, hexane, etc.), and the solution is put in a container. The solvent is removed to form a thin film on the wall of the container. The film is dried, and then a suitable aqueous solution such as a buffer solution is poured into the container to rehydrate. Ultrasonication is applied to detach the film, followed by stirring to form liposomes. The particle size of the liposome can be adjusted by passing an obtained liposome dispersion through an extruder with a filter appropriately set for pore size. Furthermore, from the liposome dispersion thus obtained, the conjugated compound not incorporated in the liposome and the lipid components may be removed by gel filtration, ultracentrifugation, dialysis, ion exchange chromatography, or the like.

In one embodiment of the invention, the weight ratio of the conjugated compound incorporated in a liposome with respect to the total weight of the lipid components (conjugated compound:lipid components) is 1:3 to 1:30, preferably 1:5 to 1:15, more preferably 1:8 to 1:12, and still more preferably 1:10.

Examples of the lipid derived from squalene as used herein include (6E,10E,14E)-2,6,10,15,19-pentamethylicosa-2,6,10,14,18-pentaene. Such compound derived from squalene can be bound appropriately via a spacer by a method well known in the art to afford a conjugated compound of the invention.

Examples of the low-molecular-weight compound of the invention, which is a TLR7 agonist that enhances the physiological activity of TLR7, include those having a molecular weight of 200 to 600, preferably a molecular weight of 250 to 500, more preferably a molecular weight of 300 to 500, and preferably those having a adenine skeleton, a pyrimidine skeleton, an imidazoquinoline skeleton, an imidazopyridine skeleton, or a quinazoline skeleton.

Examples of the compound having an adenine skeleton include compounds having a 4-amino-8-oxo-purine (8-oxoadenine) skeleton, such as compounds having a 4-amino-8-oxo-purine skeleton substituted at 9-position with an alkyl group (e.g., a straight chain alkyl group having 1 to 6 carbon atoms) which may be substituted with a 5- or 6-membered aromatic carbocyclic ring, a 5- or 6-membered aromatic heterocyclic ring or a 4- to 7-membered aliphatic nitrogen-containing heterocyclic ring. Specific examples include GSK-2245035 (2-[1(S)-methylbutoxy]-9-[5-(1-piperidinyl)pentyl]-8,9-dihydro-7H-adenin-8-one) and compounds as disclosed in WO98/01448, WO99/28321, WO02/085905, WO2008/114008, WO2008/114819, WO2008/114817, WO2008/114006, WO2010/018131, WO2010/018134, WO2008/101867, WO2010/018133 or WO2009/005687.

Examples of the compound having a pyrimidine skeleton include compounds having a 2,4-diaminopyrimidine skeleton such as for example, 2,4-diaminopyrimidines substituted appropriately at 6-position with a substituent such as alkyl group and at 5-position with an alkyl group (e.g., a straight chain alkyl group having 1 to 6 carbon atoms) which may be substituted with a 5- or 6-membered aromatic carbocyclic ring, a 5- or 6-membered aromatic heterocyclic ring or a 4- to 7-membered aliphatic nitrogen-containing heterocyclic ring. Specific examples include compounds as disclosed in WO00/12487, WO2010/133885, WO2013/172479 or WO2012/136834.

Examples of the compound having an imidazoquinoline skeleton include compounds having a 4-amino-1H-imidazo[4,5-c]quinoline skeleton, including imiquimod, resiquimod and 852A (N-[4-(4-amino-2-ethyl-1H-imidazo[4,5-c]quinolin-1-yl) butyl]methanesulfonamide), such as 4-amino-1H[4,5-c]quinoline substituted with a C1-6 alkyl group or a C1-6 alkoxy group at 1-position and with a C1-6 alkyl group or a C1-6 alkoxy group at 2-position. Specific examples include compounds as disclosed in WO2010/48520, WO2008/135791, U.S. Pat. Nos. 4,689,338, 4,698,348 or WO2007/030777.

Examples of the compound having an imidazopyridine skeleton include compounds having a 4-amino-1,3-dihydro-2H-imidazo[4,5-c]pyridin-2-one skeleton, such as compounds having a 4-amino-1,3-dihydro-2H-imidazo[4,5-c]pyridin-2-one skeleton substituted at 6- or 7-position with a C1-6 alkyl group or a C1-6 alkoxy group which may be substituted with halogen and at 1-position with an alkyl group (e.g., a straight chain alkyl group having 1 to 4 carbon atoms) which may be substituted with a 5- or 6-membered aromatic carbocyclic ring, a 5- or 6-membered aromatic heterocyclic ring or a 4- to 7-membered aliphatic nitrogen-containing heterocyclic ring. Specific examples include compounds as disclosed in WO2007/93901 and PF-4171455 (4-amino-1-benzyl-6-(trifluoromethyl)-1,3-dihydro-2H-imidazo[4,5-c]pyridin-2-one).

Examples of the compound having a quinazoline skeleton include derivatives having a 2,4-diaminoquinazoline skeleton, such as compounds having a 2,4-diaminoquinazoline skeleton substituted at 4-position with an alkyl group (e.g., a straight or branched chain alkyl group having 1 to 8 carbon atoms) which may be substituted appropriately with hydroxyl group or halogen atom. Specific examples include compounds as disclosed in WO2012/156498 or WO2014/76221.

In addition, examples of the low-molecular-weight compound which is a TLR7 agonist include besatrimod (4-amino-2-butoxy-8-[[3-[(pyrrolidin-1-yl)methyl]phenyl]methyl]-7,8-dihydropteridine-6(5H)-one) and compounds as disclosed in WO2010/077613.

Examples of the spacer in the conjugated compound of the invention include chemically stable and well-known spacers that are enabled to connect the low-molecular-weight compound and squalene or a lipid derived from squalene. Specific examples include linkers comprising one or a combination of C1-4 alkylene, amide bond, ester bond, ether bond, thioether bond, urea bond, urethane bond and sulfonamide bond.

In one embodiment of the invention, the low-molecular-weight compound of the invention that enhances the physiological activity of TLR7 comprises a structure represented by the above formula (2).

In one embodiment of the invention, the conjugated compound of the invention is a compound represented by the above formula (1) or a pharmaceutically acceptable salt thereof.

Definitions for each term in the formula (1) or formula (2) are described below.

The term "halogen atom" includes fluorine atom, chlorine atom, bromine atom, and iodine atom, and preferably, fluorine atom and chlorine atom.

The term "straight chain alkylene" includes a straight chain alkylene of 1 to 6 carbon atoms. Specific examples of the straight chain alkylene include, but are not limited to, methylene, ethylene, n-propylene and n-butylene.

The term "alkyl group" includes a straight or branched chain alkyl group of 1 to 6 carbon atoms. Specific examples of the alkyl group include, but are not limited to, methyl, ethyl, propyl, isopropyl, butyl, isobutyl, and tert-butyl.

The term "cycloalkane" includes 4- to 8-membered cycloalkanes, specifically, cyclobutane, cyclopentane, cyclohexane, cycloheptane and cyclooctane, and preferably, cyclopentane, cyclohexane and cycloheptane.

The term "divalent group derived from cycloalkane" includes, but not limited to, a divalent group capable of binding to neighboring atoms on different carbon atoms on the cycloalkane.

The term "alkoxy group" includes a straight or branched chain alkoxy group of 1 to 6 carbon atoms. Specific examples of alkoxy groups include, but are not limited to, methoxy, ethoxy, propoxy, isopropoxyl, butoxy, isobutoxy, tert-butoxy, pentoxy, and isopentoxy.

The term "4- to 8-membered nitrogen-containing saturated heterocycle" includes 4- to 8-membered nitrogen-containing saturated heterocycle containing 1 to 3 hetero atoms selected from 2 or 3 nitrogen atoms, 0 or 1 oxygen atom and 0 or 1 sulfur atom wherein at least two nitrogen atoms are contained in the ring. Specific examples include azetidine, pyrrolidine, piperidine, perhydroazepine, imidazolidine, piperazine, morpholine, thiomorpholine and perhydro-1,4-diazepine.

The "5- to 8-membered nitrogen-containing saturated heterocycle" may be 5- to 8-membered ones of the aforementioned "4- to 8-membered nitrogen-containing saturated heterocycle".

Examples of the substituent group for the nitrogen-containing saturated heterocycle include preferably methyl group, ethyl group, propyl group, hydroxymethyl group, hydroxyethyl group, carbonyl group, hydroxy group and halogen atom, and more preferably hydroxy group and halogen atom. The nitrogen-containing saturated heterocycle may be substituted with same or different 1 to 4 said substituent groups.

In the formula (1), X represents methylene, oxygen atom, sulfur atom, SO, $SO_2$ or $NR^7$ wherein $R^7$ represents hydrogen atom or an alkyl group of 1 to 3 carbon atoms. $R^7$ preferably represents hydrogen atom or methyl group. X preferably represents methylene.

In the formula (1), $R^1$ preferably represents hydrogen atom or an alkyl group of 1 to 4 carbon atoms. Specific examples of $R^1$ include methyl group, ethyl group, propyl group and butyl group.

In the formula (1), $R^2$ represents hydrogen atom or a substituted or unsubstituted alkyl group of 1 to 4 carbon atoms. When the alkyl group is substituted, specific examples of the substituent group include hydroxy group. Specific examples of $R^2$ include hydrogen atom, methyl group, ethyl group, propyl group, hydroxymethyl group and hydroxyethyl group.

In the formula (1), $R^3$ preferably represents an alkyl group of 1 to 4 carbon atoms, an alkoxy group of 1 to 4 carbon atoms or an alkylthio group of 1 to 4 carbon atoms, more preferably an alkyl group of 1 to 3 carbon atoms or an alkoxy group of 1 to 3 carbon atoms. Specific examples of $R^3$ include methyl group, ethyl group, propyl group and butyl group, and more preferably methyl group.

In the formula (1), examples of $R^4$ include preferably hydrogen atom, an alkyl group of 1 to 3 carbon atoms, an alkoxy group of 1 to 3 carbon atoms, hydroxy and halogen atom, and more preferably hydrogen atom and methoxy group.

In the formula (1), $Y^1$ preferably represents a single bond, —$(CR^9R^{10})_p$— or —$(CR^9R^{10})_r$—O—$(CR^{9'}R^{10'})_{r'}$— wherein $R^9$, $R^{10}$, $R^{9'}$ and $R^{10'}$ are independently hydrogen atom or an alkyl group of 1 to 4 carbon atoms. $R^9$, $R^{10}$, $R^{9'}$ and $R^{10'}$ are preferably independently hydrogen atom or methyl group, more preferably hydrogen atom. More preferably, $Y^1$ is a single bond or —$(CR^9R^{10})_p$—.

In the formula (1), when $Y^1$ is —$(CR^9R^{10})_p$—, p is preferably an integer of 1 to 4, more preferably 1, 2 or 3.

In the formula (1), when $Y^1$ represents —CH=CH— $(CR^9R^{10})_q$— or

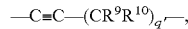 [Chem. 5]

q and q' are preferably independently an integer of 0 to 3, more preferably 0 or 1.

In the formula (1), when $Y^1$ represents —$(CR^9R^{10})_r$—O—$(CR^{9'}R^{10'})_{r'}$—, r is preferably an integer of 0 to 3 and r' is preferably 1 to 4, provided that the sum of r and r' is 5 or less, and more preferably r is 0 or 1 and r' is 1 or 2.

In the formula (1), when $Y^1$ is a single bond or —$(CR^9R^{10})_p$—, $Y^2$ represents a single bond or —C(O)- (carbonyl).

In a preferred embodiment, $Y^1$ represents a single bond and $Y^2$ represents —C(O)—.

In a preferred embodiment, $Y^1$ represents —$(CR^9R^{10})_p$— and $Y^2$ represents a single bond wherein $R^9$ and $R^{10}$ are preferably independently hydrogen atom or methyl group, more preferably hydrogen atom, and p is preferably an integer of 1 to 4, more preferably 1, 2 or 3.

In one embodiment of the present invention, L in the formula (1) is a straight chain alkylene of 2 to 4 carbon atoms, preferably straight chain alkylene of 2 or 3 carbon atoms, and more preferably ethylene.

In one embodiment of the invention, L in the formula (1) represents a divalent group derived from 4- to 8-membered cycloalkane, more preferably a divalent group derived from 5- or 6-membered cycloalkane. Specific examples of the divalent group include the following divalent groups.

[Chem. 6]

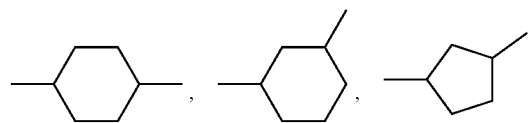

In one embodiment of the invention, $R^5$ and $R^6$ in the formula (1) represents hydrogen atom or a substituted or unsubstituted alkyl group of 1 to 3 carbon atoms, preferably independently hydrogen atom or an alkyl group of 1 to 3 carbon atoms, more preferably independently hydrogen atom or methyl group, and still more preferably hydrogen atom. When the alkyl group is substituted, it is substituted with 1 to 4 same or different substituents selected from hydroxy group or halogen atom.

In one embodiment of the invention, either $R^5$ or $R^6$ in the formula (1) may be taken together with any carbon atom of L to form a 4- to 8-membered nitrogen-containing saturated heterocycle, preferably a 4- to 6-membered nitrogen-containing saturated heterocycle. Specific examples of the 4- to 8-membered nitrogen-containing saturated heterocycle formed by $R^5$ in combination with any carbon atom of L include the followings.

[Chem. 7]

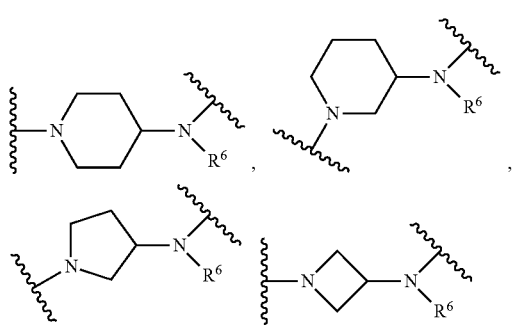

wherein $R^6$ represents hydrogen atom or a substituted or unsubstituted alkyl group of 1 to 6 carbon atoms.

Specific examples of the 4- to 8-membered nitrogen-containing saturated heterocycle formed by $R^6$ in combination with any carbon atom of L include the followings.

[Chem. 8]

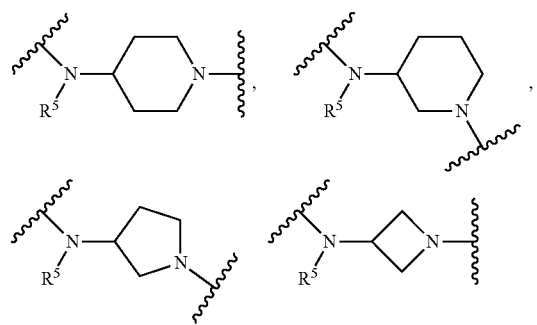

wherein $R^5$ represents hydrogen atom or a substituted or unsubstituted alkyl group of 1 to 6 carbon atoms.

In one embodiment of the invention, $R^5$ and $R^6$ in the formula (1) may be taken together to form a substituted or unsubstituted 5- to 8-membered nitrogen-containing saturated heterocycle, preferably 5- or 6-membered nitrogen-containing saturated heterocycle. Specific examples of such nitrogen-containing saturated heterocycle include the nitrogen-containing saturated heterocycles of the following formulae:

[Chem. 9]

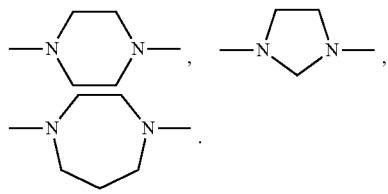

When either $R^5$ or $R^6$ is taken together with any carbon atom of L to form a substituted 4- to 8-membered nitrogen-containing saturated heterocycle or when $R^5$ and $R^6$ are taken together to form a substituted 5- to 8-membered nitrogen-containing saturated heterocycle, the substituent group are preferably same or different 1 to 4 substituents selected from hydroxy group or a halogen atom.

In the formula (1), m preferably represents 1.

In a preferred embodiment, the compound of the formula (1) is a compound wherein
  X represents methylene,
  $R^1$ represents an alkyl group of 1 to 4 carbon atoms,
  $R^2$ represents hydrogen atom, an alkyl group of 1 to 3 carbon atoms, or an alkyl group of 1 to 3 carbon atoms substituted with hydroxy group,
  $R^3$ represents an alkyl group of 1 to 3 carbon atoms or an alkoxy group of 1 to 3 carbon atoms,
  $R^4$ represents hydrogen atom, halogen atom, hydroxy group, an alkyl group of 1 to 6 carbon atoms or an alkoxy group of 1 to 6 carbon atoms,
  $Y^1$ represents a single bond or $-(CR^9R^{10})_p-$,
  $Y^2$ represents $-C(O)-$,
  L represents a straight chain alkylene of 2 to 6 carbon atoms,
  $R^5$ and $R^6$ independently represent hydrogen atom or an alkyl group of 1 to 3 carbon atoms or either $R^5$ or $R^6$ is taken together with any carbon atom of L to form a 4- to 8-membered nitrogen-containing saturated heterocycle or $R^5$ and $R^6$ are taken together to form a substituted or unsubstituted 4- to 8-membered nitrogen-containing saturated heterocycle, m represents 0 or 1, preferably 1.

In a preferred embodiment, the compound of the formula (1) is a compound wherein
  X represents methylene,
  $R^1$ represents an alkyl group of 1 to 4 carbon atoms,
  $R^2$ represents hydrogen atom, an alkyl group of 1 to 3 carbon atoms, or an alkyl group of 1 to 3 carbon atoms substituted with hydroxy group,
  $R^3$ represents an alkyl group of 1 to 3 carbon atoms or an alkoxy group of 1 to 3 carbon atoms,
  $R^4$ represents hydrogen atom, halogen atom, hydroxy group, an alkyl group of 1 to 6 carbon atoms or an alkoxy group of 1 to 6 carbon atoms,
  $Y^1$ represents $-(CR^9R^{10})_p-$
  $Y^2$ represents a single bond,
  L represents a straight chain alkylene of 2 to 6 carbon atoms,
  $R^5$ and $R^6$ independently represent hydrogen atom or an alkyl group of 1 to 3 carbon atoms or either $R^5$ or $R^6$ is taken together with any carbon atom of L to form a 4- to 8-membered nitrogen-containing saturated heterocycle or $R^5$ and $R^6$ are taken together to form a substituted or unsubstituted 4- to 8-membered nitrogen-containing saturated heterocycle, m represents 0 or 1, preferably 1.

In a preferred embodiment, the compound of the formula (1) is a compound wherein X represents methylene, $R^1$ represents an alkyl group of 1 to 4 carbon atoms, $R^2$ represents hydrogen atom, an alkyl group of 1 to 3 carbon atoms, or an alkyl group of 1 to 3 carbon atoms substituted with hydroxy group, $R^3$ represents an alkyl group of 1 to 3 carbon atoms or an alkoxy group of 1 to 3 carbon atoms, $R^4$ represents hydrogen atom, halogen atom, hydroxy group, an alkyl group of 1 to 6 carbon atoms or an alkoxy group of 1 to 6 carbon atoms, $Y^1$ represents a single bond and $Y^2$ represents —C(O)—, or $Y^1$ represents —$(CR^9R^{10})_p$— and $Y^2$ represents a single bond, L represents a straight chain alkylene of 2 to 6 carbon atoms, $R^5$ and $R^6$ independently represent hydrogen atom or an alkyl group of 1 to 3 carbon atoms, m represents 0 or 1, preferably 1.

Examples of preferred conjugated compounds of the invention include the following compounds or pharmaceutically acceptable salts thereof:

(4E,8E,12E,16E,20E)-N-{2-[{4-[(2-amino-4-{[1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;

(4E,8E,12E,16E,20E)-1-(4-{4-[(2-amino-4-{[1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;

(4E,8E,12E,16E,20E)-1-(4-{4-[(2-amino-4-{[1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;

4-[(2-amino-4-{[1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and 4-[(2-amino-4-{[1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide.

Alternatively, (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and 4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide.

Examples of the pharmaceutically acceptable salt of the compound of the formula (1) as used herein include acid addition salts or base addition salts of the compound of the formula (1). Examples of the acid addition salt include acid addition salts with inorganic or organic acids such as hydrochloric acid, hydrobromic acid, sulfuric acid, trifluoroacetic acid, citric acid and maleic acid. Examples of the base addition salt include alkali metal salts such as sodium salt and potassium salt, alkaline earth metal salts such as calcium salt, and ammonium salt.

The compound of the formula (1) can be prepared by the following processes using a known compound as a starting material.

The starting material may be used as a salt. Also, the following processes are merely illustrative, and the compound may be produced by another process appropriately based on the knowledge of one skilled in organic synthesis.

[Process 1 for the Preparation of Compound (1)]

A compound of the formula (1) or a salt thereof can be prepared, for example, by the following process.

[Chem. 10]

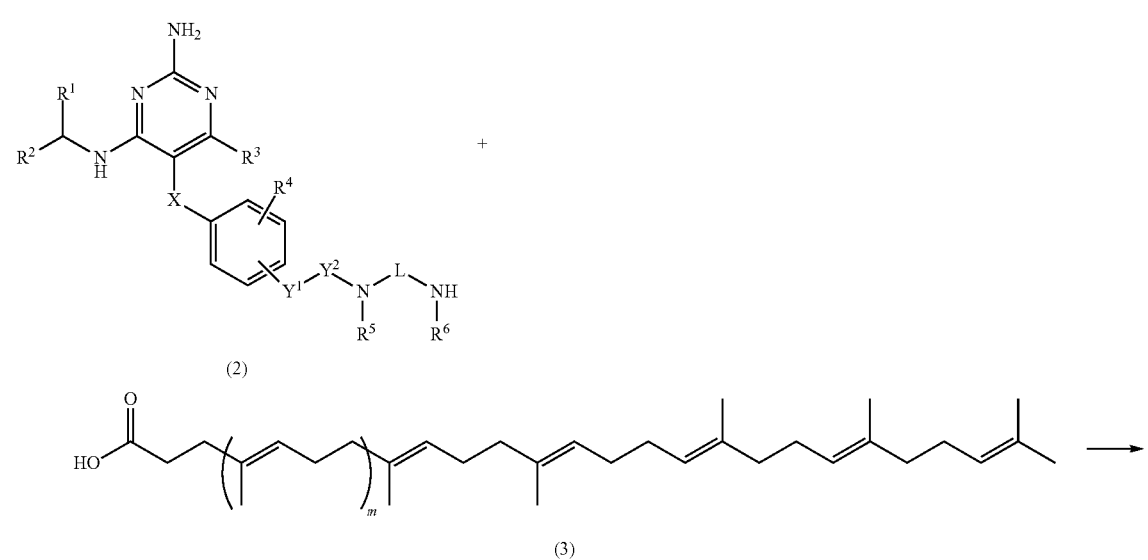

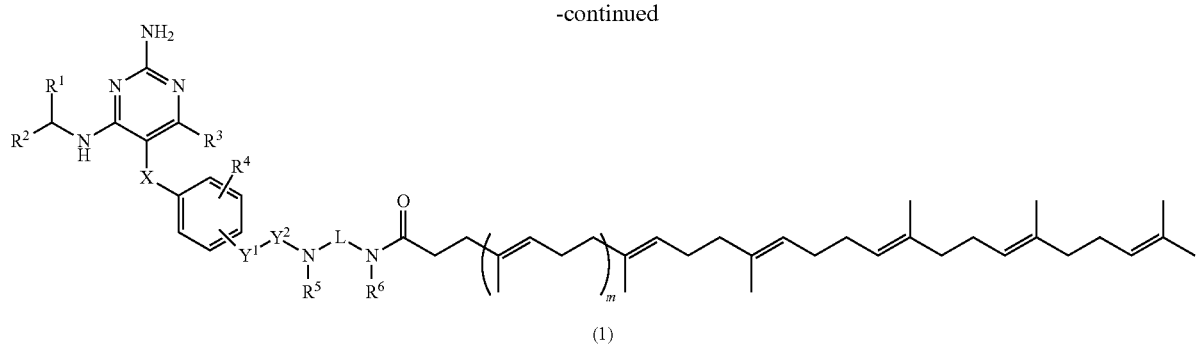

(1)

Compound (1) can be prepared by reacting compound (3) with compound (2) in an inert solvent, using a condensing agent, optionally in the presence of a base.

The base is not limited as long as it is used by a person skilled in the art in organic chemical reactions, and examples include organic bases such as N-methyl morpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine and picoline; and inorganic bases such as sodium bicarbonate, potassium bicarbonate, sodium carbonate and potassium carbonate. The base may be used generally in an amount of 0.1 to 100 equivalents, preferably 1 to 5 equivalents, to the compound (3).

The condensing agent may be those described in Experimental Chemistry Course, Vol. 22, edited by The Chemical Society of Japan, Maruzen Co., Ltd., and examples include phosphoric acid esters such as diethyl cyanophosphate and diphenylphosphoryl azide; carbodiimides such as 1-ethyl-3-(3-diethylaminopropyl)-carbodiimide hydrochloride (WSC.HCl) and dicyclohexylcarbodiimide (DCC); combinations of a disulfide such as 2,2'-dipyridyl disulfide and a phosphine such as triphenylphosphine; phosphorus halides such as N,N'-bis(2-oxo-3-oxazolidinyl)phosphinic chloride (BOPCl); combinations of an azodicarboxylic acid diester such as diethyl azodicarboxylate and a phosphine such as triphenylphosphine; 2-halo-1-lower alkylpyridinium halides such as 2-chloro-1-methylpyridinium iodide; 1,1'-carbonyldiimidazole (CDI); diphenylphosphoryl azide (DPPA); diethylphosphoryl cyanide (DEPC); tetrafluoroborates such as 2-(1H-benzotriazole-1-yl)-1,1,3,3-tetramethyluronium tetrafluoroborate (TBTU) and 2-chloro-1,3-dimethylimidazolidinium tetrafluoroborate (CIB); phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino)phosphonium hexafluorophosphate (PYBOP), and 2-(7-aza-1H-benzotriazol-1-yl)-1,1,3,3-tetramethyluronium hexafluorophosphate (HATU).

Examples of the inert solvent include ether solvents such as tetrahydrofuran, diethyl ether, 1,4-dioxane, 1,2-dimethoxyethane; hydrocarbon solvents such as hexane, heptane, toluene, benzene and xylene; halogenated hydrocarbon solvents such as dichloromethane, chloroform and dichloroethane; ketone solvents such as acetone; aprotic solvents such as acetonitrile, N,N'-dimethylformamide, dimethylsulfoxide and hexamethylphosphoramide; and a mixture thereof. The reaction temperature is preferably selected from, but not limited to, the range of about −70° C. to 100° C., more preferably 0° C. to 40° C.

Alternatively, Compound (3) may be converted to an acid halide using a halogenating agent (e.g., 1-chloro-N,N,2-trimethylpropenylamine, phosphorus oxychloride, phosphorus trichloride, thionyl chloride, phosphorus pentachloride) and then reacted with Compound (2) in an inert solvent, optionally in the presence of a base, to obtain Compound (1).

Examples of the inert solvent include ether solvents such as tetrahydrofuran, diethyl ether, 1,4-dioxane, 1,2-dimethoxyethane; hydrocarbon solvents such as hexane, heptane, toluene, benzene and xylene; halogenated hydrocarbon solvents such as dichloromethane, chloroform and dichloroethane; ester solvents such as ethyl acetate and isopropyl acetate; ketone solvents such as methylethyl ketone and acetone; and aprotic solvents such as acetonitrile, N,N'-dimethylformamide, dimethylsulfoxide and hexamethylphosphoramide. Examples of the base include organic bases such as N-methyl morpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, picoline. The halogenating agent can be used in an amount of 0.1 to 100 equivalents, preferably 0.8 to 3 equivalents, to the compound (3). The reaction temperature is preferably selected from, but not limited to, the range of about −30° C. to 60° C.

Compound (3) can be prepared according to a method well known in the art (see Org. Biomol. Chem. 2011, 9, 4367).

[Process 1 for the Preparation of Compound (2)]

Compound (2a), wherein $Y^2$ in the formula (2) is —C(O)—, or a salt thereof can be prepared by the following process.

[Chem. 11]

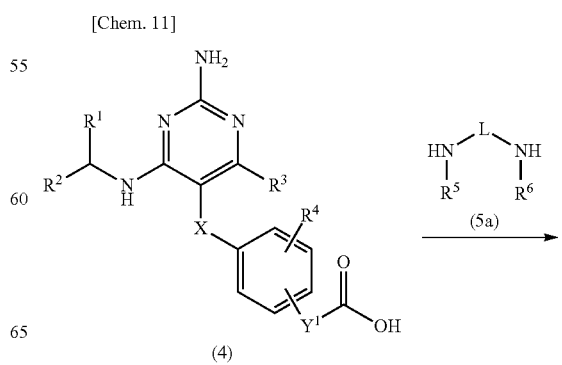

(4)

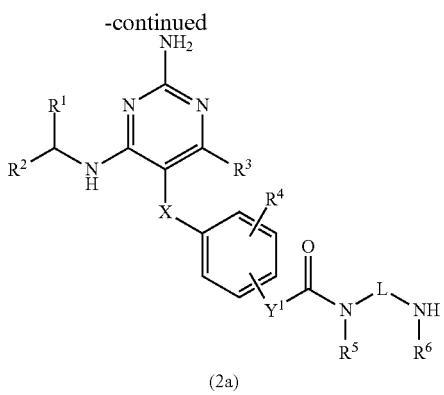

(2a)

wherein X, $R^1$, $R^2$, $R^3$, $R^4$, $R^5$, $R^6$, $Y^1$ and L are as defined above.

Compound (2a) can be synthesized from Compound (4) and Compound (5a) according to a method as described for the preparation of Compound (1).

Compound (4) can be prepared according to a method well known in the art, such as those described in WO 2009/067081 and WO 2010/103885.

[Process 2 for the Preparation of Compound (2)]

Compound (2b), wherein $Y^2$ in the formula (2) is a single bond, or a salt thereof can be prepared, for example, by the following process.

[Chem. 12]

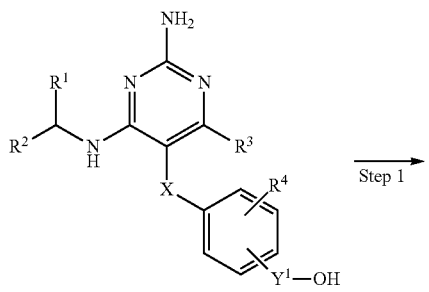

(6)

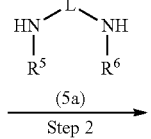

(2b)

wherein X, $R^1$, $R^2$, $R^3$, $R^4$, $R^5$, $R^6$ and L are as defined above, $Y^1$ is —$(CR^9R^{10})_p$—, —CH=CH—$(CR^9R^{10})_q$—, or —C≡C—$(CR^9R^{10})_{q'}$— [Chem. 13]

wherein p, q and q' are as defined above, and
(1) $Q^1$ represents —$Y^1NHR^5$ and $Q^2$ represents CHO; or
(2) $Q^1$ represents —$Y^{1'}$—CHO, wherein is absent or represents alkylene and —$Y^{1'}$—$(CR^9R^{10})$— corresponds to —$Y^1$—, and $Q^2$ represents —$CH_2NHR^5$.

Compound (2b) can be prepared by coupling Compound (6) and Compound (5b) under a condition for reductive amination well known in the art. Specifically, an aldehyde compound and an amine compound can be reacted in a solvent with a reducing agent, such as sodium triacetoxyborohydride and sodium cyanoborohydride, in the presence or absence of an acid such as acetic acid to prepare Compound (2b).

Compound (6) can be prepared according to a method well known in the art, such as those described in WO2010/133885, WO2012/066335, and WO2012/066336.

[Process 3 for the Preparation of Compound (2)]

Also, Compound (2b) or a salt thereof can be prepared according to the following process.

[Chem. 14]

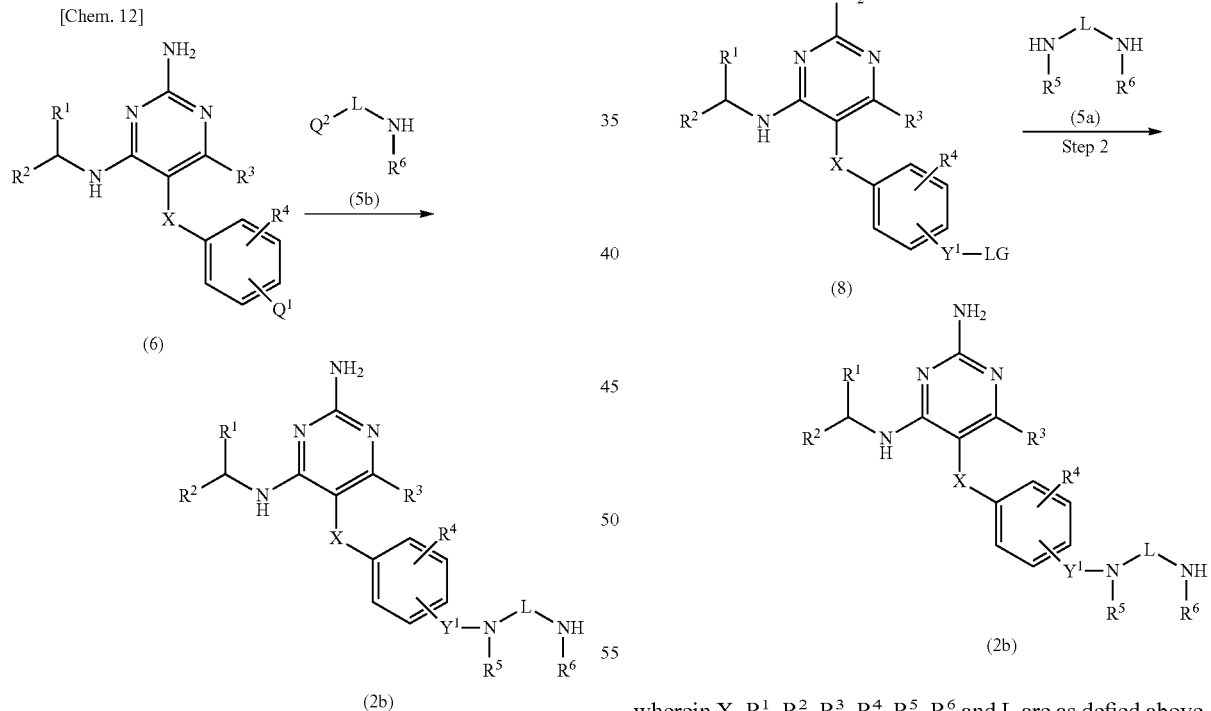

wherein X, $R^1$, $R^2$, $R^3$, $R^4$, $R^5$, $R^6$ and L are as defied above, and $Y^1$ is —$(CR^9R^{10})_p$—), —CH=CH—$(CR^9R^{10})_q$—, —C≡C—$(CR^9R^{10})_{q'}$— [Chem. 15]

or —$(CR^9R^{10})_r$—O—$(CR^{9'}R^{10'})_{r'}$—, wherein $R^9$, $R^{10}$, $R^{9'}$, $R^{10'}$, p, q, q', r and r' are as defined above, and LG is a leaving group.

Step 1

Compound (7) can be prepared according to a method well known in the art (see WO 2010/133885, WO 2012/066336, etc.). The leaving group LG in Compound (8) is not limited so long as it is well known as a leaving group in the art, and a halogen atom, an alkylsulfonyloxy group, an arylsulfonyloxy group, or the like can be used appropriately. Compound (8) can be prepared by reacting Compound (7) with methanesulfonyl chloride, p-toluenesulfonyl chloride or the like, in the presence of a base such as triethylamine, diisopropylethylamine, pyridine, dimethylaminopyridine, sodium carbonate, potassium carbonate or the like. The reaction temperature is preferably selected from, but not limited to, the range of about 0° C. to 120° C.
Step 2
Compound (2b) can be prepared by reacting Compound (8) with Compound (5a) in an inert solvent in the presence of a base.

The base is not limited so long as it is used as a base in a usual reaction, and examples include organic bases such as N-methyl morpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine; inorganic bases such as sodium bicarbonate, potassium bicarbonate, sodium carbonate, potassium carbonate, cesium carbonate, sodium hydroxide and sodium hydride. The base may be used generally in an amount of 0.1 to 100 equivalents, preferably 1 to 3 equivalents, to Compound (8).

Examples of the inert solvent include ether solvents such as tetrahydrofuran, diethyl ether, 1,4-dioxane, 1,2-dimethoxyethane; hydrocarbon solvents such as hexane, heptane, toluene, benzene and xylene; aprotic solvents such as acetonitrile, N,N'-dimethylformamide, N-methyl pyrrolidone, dimethylsulfoxide; and a mixture thereof. The reaction temperature is preferably selected from, but not limited to, the range of about 0° C. to 120° C.
[Process 4 for the Preparation of Compound (2)]
Also, Compound (2b) or a salt thereof can be prepared according to the following process.

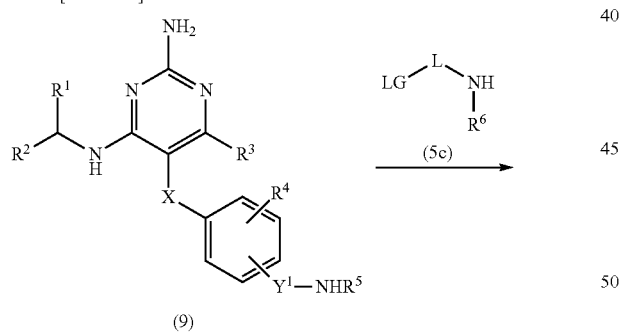

wherein X, $R^1$, $R^2$, $R^3$, $R^4$, $R^5$ and $R^6$ are as defined above, L is substituted or unsubstituted alkylene of 2 to 6 carbon atoms, $Y^1$ is a single bond, $-(CR^9R^{10})_q-$, $-CH=CH-(CR^9R^{10})_q-$, $$-C\equiv C-(CR^9R^{10})_{q'}-$$ [Chem. 17]

or $-(CR^9R^{10})_r-O-(CR^{9'}R^{10'})_{r'}-$, wherein $R^9$, $R^{10}$, $R^{9'}$, $R^{10'}$, q, q', r and r' are as defined above, and LG is a leaving group.

Compound (2b) can be prepared in the similar manner as described in Step 2 of Process 3 for the preparation of Compound (2), using Compound (9) and Compound (5c).

Compound (9) can be prepared according to a method well known in the art, such as those described in WO2010/133885, and WO2012/066336.
[Process 5 for the Preparation of Compound (2)]
Compound (2c) or a salt thereof can be prepared according to the following process.

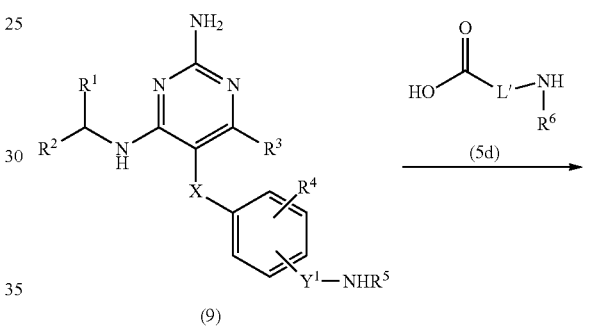

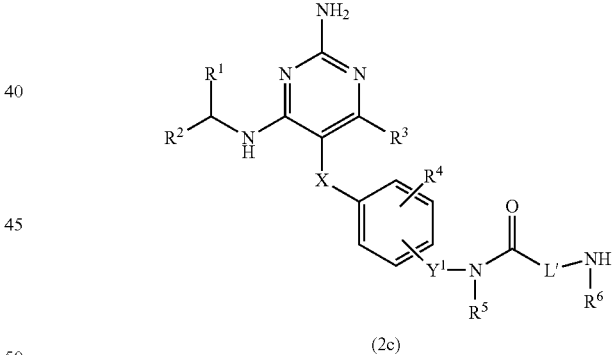

wherein X, $R^1$, $R^2$, $R^3$, $R^4$, $R^5$ and $R^6$ are as defined above, L' is substituted or unsubstituted alkylene of 1 to 5 carbon atoms, $Y^1$ is a single bond, $-(CR^9R^{10})_p-$, $-CH=CH-(CR^9R^{10})_q-$, $$-C\equiv C-(CR^9R^{10})_{q'}-$$ [Chem. 19]

or $-(CR^9R^{10})_r-O-(CR^{9'}R^{10'})_{r'}-$ wherein $R^9$, $R^{10}$, $R^{9'}$, $R^{10'}$, p, q, r and r' are as defined above.

Compound (2c) can be prepared as described in the process for the preparation of Compound (1), using Compound (9) and Compound (5d).

The present invention provides intermediates in the processes described above. Specifically, such intermediates may be a compound of the formula (2):

[Chem. 20]

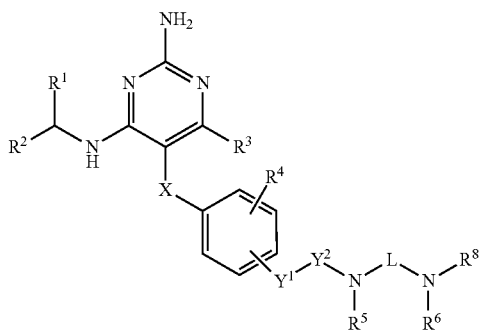

wherein

X is methylene, oxygen atom, sulfur atom, SO, $SO_2$ or $NR^7$ wherein $R^7$ is hydrogen atom or an alkyl group of 1 to 3 carbon atoms;

$R^1$ and $R^2$ are independently hydrogen atom or a substituted or unsubstituted alkyl group of 1 to 6 carbon atoms, provided that when the alkyl group is substituted, it is substituted with 1 to 4 same or different substituents selected from the group consisting of hydroxy group, halogen atom and an alkoxy group of 1 to 6 carbon atoms;

$R^3$ is an alkyl group of 1 to 6 carbon atoms, an alkoxy group of 1 to 6 carbon atoms or an alkylthio group of 1 to 6 carbon atoms;

$R^4$ is hydrogen atom, halogen atom, hydroxy group, an alkyl group of 1 to 6 carbon atoms, an alkoxy group of 1 to 6 carbon atoms or cyano group;

$Y^1$ is a single bond, $—(CR^9R^{10})_p—$, $—CH=CH—(CR^9R^{10})_q—$,

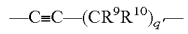

or $—(CR^9R^{10})_r—O—(CR^{9'}R^{10'})_{r'}—$ wherein $R^9$, $R^{10}$, $R^{9'}$, $R^{10'}$ are independently hydrogen atom or an alkyl group of 1 to 4 carbon atoms;

$Y^2$ is a single bond or $—C(O)—$;

L is a substituted or unsubstituted straight chain alkylene of 2 to 6 carbon atoms or a divalent group derived from 4- to 8-membered cycloalkane, provided that when the straight chain alkylene or the cycloalkane is substituted, it is substituted with 1 to 4 same or different substituents selected from the group consisting of alkyl group of 1 to 5 carbon atoms, hydroxy group and halogen atom, and any one of the methylene group in the straight chain alkylene of L is optionally replaced with carbonyl group;

$R^5$ and $R^6$ are independently hydrogen atom or a substituted or unsubstituted alkyl group of 1 to 6 carbon atoms, or either $R^5$ or $R^6$ is taken together with any carbon atom of L to form a 4- to 8-membered nitrogen-containing saturated heterocycle, or $R^5$ and $R^6$ are taken together to form a substituted or unsubstituted 5- to 8-membered nitrogen-containing saturated heterocycle; provided that when the alkyl group is substituted, it is substituted with same or different 1 to 4 groups selected from the group consisting of hydroxy group and halogen atom; when the 4- to 8-membered nitrogen-containing saturated heterocycle or the 5- to 8-membered nitrogen-containing saturated heterocycle is substituted, it is substituted with same or different 1 to 4 groups selected from the group consisting of methyl group, ethyl group, propyl group, hydroxymethyl group, hydroxyethyl group, carbonyl group, hydroxy group and halogen atom;

p is an integer of 1 to 6;

q and q' are independently an integer of 0 to 4;

r is an integer of 0 to 5, and r' is an integer of 1 to 5, provided that the sum of r and r' is 5 or less and provided that r' is an integer of 2 or more when $Y^2$ is a single bond; and $R^8$ is hydrogen atom or an amino protecting group, and salts thereof.

The protecting group of $R^8$ in the formula (2) may be, but not limited to, a group commonly used as a protecting group for amino group. Specific examples include carbamates such as t-butoxycarbonyl group, benzyloxycarbonyl group and 9-fluorenylmethyloxycarbonyl group; benzyl group; sulfones such as nosyl group; imides such as phthalimide.

In a process of the invention, if a specific functional group, such as hydroxy group or amino group, in a reagent is necessary to be protected, protection/deprotection may be conducted with one or more protecting group at an appropriate step in the process according to a procedure well known in the art.

The protection/deprotection of functional groups is described in J. W. F. McOmie, Ed., "Protective Groups in Organic Chemistry", Plenum Press (1973) and T. W. Greene and P. G. M. Wuts, "Protective Groups in Organic Synthesis," 3rd Edition, Wiley-Interscience (1999).

Those skilled in the art can prepare the conjugated compound of the invention according to a process analogous to that described above appropriately in combination with organic synthesis techniques well known in the art.

In case where the conjugated compound of the invention exists in an optically active or a racemic form by virtue of one or more asymmetric carbon atoms, the present disclosure includes in its scope such optically active or racemic form having a physiological activity as described below. The synthesis of such optically active forms may be carried out by standard techniques of organic chemistry well known in the art, for example, a synthesis from optically active starting materials or a resolution of a racemic mixture. The physiological activity may be evaluated using a standard laboratory technique as described below.

The conjugated compound of the invention may exist in an unsolvated or solvated form such as a hydrate.

Also, the conjugated compound of the invention may be deuterated form, wherein one or more $^1H$ are replaced with $^2H(D)$.

The form of the conjugated compound of the invention may be, but not limited to, amorphous or exist as a crystal. Crystal polymorphism may be present in a crystalline compound of the formula (1) or a pharmaceutically acceptable salt thereof, and thus, the compound of the present invention includes those in any crystal form.

In one embodiment of the invention, there is provided a composition, in particular a pharmaceutical composition, comprising a liposome of the invention.

The composition can be used as an adjuvant for maintaining or enhancing an immunostimulatory activity of an active ingredient having the immunostimulatory activity.

That is, the composition comprising a liposome of the invention has an activity of inducing or enhancing an antigen-specific antibody, specifically an antigen-specific IgG, more specifically a Th1 type antigen-specific IgG (e.g., IgG2c).

In addition, the composition comprising a liposome of the present invention has an activity of inducing or enhancing CD4-positive (i.e., MHC class 2-restricted) and/or CD8-positive (i.e., MHC Class 1-restricted) T lymphocytes.

Furthermore, the composition comprising a liposome of the present invention has an activity of inducing or enhancing MHC-restricted antigen-specific T lymphocytes.

Also, the composition comprising a liposome of the present invention has an activity of inducing or enhancing memory T lymphocytes, specifically CD8-positive effector memory T lymphocytes.

The composition comprising a liposome of the present invention may contain an antigen. Examples of the antigen include a tumor antigen protein; a tumor antigen peptide derived from said tumor antigen protein, such as NY-ESO-1, MAGE-3, WT1 and Her2/neu; a hypervariable region of an antibody; and a pathogen-derived antigen such as a protein or a partial peptide thereof derived from a virus or a bacterium. Also, a complex of such antigen and a carrier is included in the scope of the antigen as used herein. Examples of such complex include those wherein an antigen (including, but not limited to, proteins and peptides) are chemically bound to a protein that serves as a carrier via a linker well known in the art; and those wherein an antigen is contained in a virus-like particle (VLP). Therefore, the composition comprising a liposome of the present invention, by using in combination with the above-mentioned antigen, is useful as a drug for the treatment or prevention of cancer, infection with virus or bacteria.

Also, the composition comprising a liposome of the present invention can be used as an adjuvant to assist immunostimulation in a treatment for inducing other immunological or immune reaction. Specific Examples of the treatment include ex vivo and in vivo approaches to enhance the immunogenicity of tumor cells of a patient (e.g., transfection with cytokines such as interleukin 2, interleukin 4 or granulocyte macrophage colony stimulating factor), approaches to reduce T cell anergy, approaches using transfected immune cells (e.g., cytokine-transfected dendritic cells), approaches using cytokine-transfected tumor cell lines, approaches to reduce the function of immunosuppressive cells (e.g., regulatory T cells, bone marrow-derived repressed cells and IDO (indoleamine 2,3-dioxygenase)-expressing dendritic cells), and radiation therapy to induce an immune response.

Examples of the administration route of the composition includes parenteral administration, specifically intravascular (e.g., intravenous), subcutaneous, intradermal, intramuscular, intranasal, and percutaneous administrations.

In one embodiment, the composition comprising a liposome of the present invention may contain the liposome of the invention and a pharmaceutically acceptable diluent, antioxidant agent, stabilizer, sugar, buffer or carrier in an amount which does not substantially affect the stability of the liposome and the efficacy of the conjugated compound.

The dosage form of the composition of the present invention may be a liquid formulation for injection or nasal drops or a freeze-dried formulation prepared by lyophilizing the liquid formulation.

Examples of the liquid formulation for injection include aqueous suspension formulations wherein the liposome of the invention is dispersed in water.

Examples of the liquid formulation for nasal drops include aqueous suspension formulations wherein the liposome of the invention is dispersed in water.

The aqueous solution or aqueous suspension formulation may be an aqueous solution or aqueous suspension containing distilled water for injection, and appropriately, a buffer, a pH adjusting agent, a stabilizer, an isotonizing agent or an emulsifying agent.

Examples of the buffering agent include phosphate and organic acid salt.

In preparation of a freeze-dried formulation, an excipient may be added as appropriate. The excipient and its amount are not limited so long as they are preferable to form good freeze-dried cake or lyophilized powder, and examples include saccharides, sugar alcohols, amino acids and sodium chloride, for example, 0.1 to 20% mannitol.

The composition of the present invention may further contain other additives, and examples of such additives include antioxidants, preservatives, and soothing agents.

The liposome of the invention may be administered simultaneously with or at any interval before or after the antigenic substance (immunogen) in a unit dose ranging from generally 5 to 5000 mg/m$^2$ of body surface area, i.e., about 0.1 ng/kg to 100 mg/kg, which provides a prophylactically or therapeutically effective dose. The unit dosage form for injections, tablets or capsules generally contains, for example, liposomes containing 1 ng to 250 mg of the conjugated compound of the invention, and preferably, used at a dose ranging from 1 ng to 50 mg/kg of the conjugated compound per day. However, the daily dose may vary depending on the host to be treated, the route of administration and the severity of the disease being treated. Thus, the optimal dose can be determined by a practitioner who treats individual patient or warm-blooded animal.

The term "treatment" as used herein means alleviating some or all of the symptoms of disease, in whole or in part, or preventing or delaying the progression of disease.

The term "prevention" as used herein means primary prevention of disease (prevention of onset of disease) or secondary prevention of disease (prevention of relapse in a patient whose symptom has been alleviated or disease has been cured after the onset of the disease, prevention of recurrence).

Since the liposome of the present invention has an immune adjuvant activity in vitro or in vivo, it is useful as a vaccine adjuvant for maintaining or enhancing the immunogenicity of the antigen.

The liposome of the present invention can be used for maintaining or enhancing the effect of an immuno-stimulating substance (immunostimulatory substance) which is an agent for treating or preventing a disease, i.e., the action of a substance inducing an antigen-specific immune reaction.

A composition comprising the liposome of the invention and a substance enhancing an antigen-specific immune reaction (also referred to as an antigen) is also an embodiment of the present invention. The antigen may be, but not limited to, an antigen protein, an antigen peptide (partial peptide) derived from said antigen protein, or a complex thereof with a carrier.

In a certain embodiment of the invention, the liposome of the invention can be administered in combination with a tumor antigen protein or a tumor antigen peptide for cancer immunotherapy to treat or prevent cancer. Examples of the cancer include common cancers such as bladder cancer, head and neck cancer, prostate cancer, breast cancer, lung cancer, ovarian cancer, pancreatic cancer, cancer of intestine and colon, stomach cancer, skin cancer and brain cancer; malignant diseases (Hodgkin's lymphoma and non-Hodgkin's lymphoma, etc.) that affect bone marrow (including leukemia) and lymphoproliferative system. The treatment or prevention of cancer as used herein may be prevention of metastatic disease and tumor recurrence, and prevention and treatment of paraneoplastic syndrome.

Examples of the antigen include, but not limited to, MAGE (Science, 254: p 1643 (1991)), gp 100 (J. Exp. Med., 179: p 1005 (1994)), MART-1 (Proc. Natl. Acad. Sci. USA, 91: p 3515 (1994)), tyrosinase (J. Exp. Med., 178: p 489 (1993)), MAGE related proteins (J. Exp. Med., 179: p 921 (1994)), β-catenin (J. Exp. Med., 183: p 1185 (1996)), CDK4 (Science, 269: p 1281 (1995)), HER2/neu (J. Exp. Med., 181: p 2109 (1995)), mutant p 53 (Proc. Natl. Acad. Sci. USA, 93: p 14704(1996)), CEA (J. Natl. Cancer. Inst., 87: p 982 (1995)), PSA (J. Natl. Cancer. Inst., 89: p 293 (1997)), WT1 (Proc. Natl. Acad. Sci. USA, 101: p 13885 (2004)), HPV-derived antigen (J. Immunol., 154: p 5934 (1995)), and EBV-derived antigen (Int. Immunol., 7: p 653 (1995)).

Examples of the tumor antigen peptide derived from the cancer antigen include, but not limited to, MAGEA3 peptide 168-176 (Coulie P G et al., Immunol. Rev. 188: 33 (2002)), gp 100 peptide 209-217 (Rosenberg S A et al., Nat. Med. 4: 321 (1998)), gp 100 peptide 280-288 (Phan G Q et al., Proc. Natl. Acad. Sci. USA 100: 8372 (2003)), Melan-A peptide 27-35 (Cormier J N et al., Cancer J. Sci. Am. 3: 37 (1997)), Melan-A peptide 26-35, Tyrosinase peptide 1-9, Tyrosinase peptide 368-376, gp 100 peptide 280-288, gp 100 peptide 457-466 (Jager E et al., Int. J. Cancer 67: 54 (1996)), HER-2 peptide 369-384, HER-2 peptide 688-703, HER-2 peptide 971-984 (Knutson K L et al., J. Clin. Invest. 107: 477 (2001)), and MAGE-A12 peptide 170-178 (Bettinotti M P et al., Int. J. Cancer 105: 210 (2003)).

In addition, the liposome of the present invention, by administering in combination with an active ingredient of a vaccine for preventing infectious diseases, can prevent various infectious diseases such as genital wart, common wart, plantar wart, hepatitis B, hepatitis C, herpes simplex virus, molluscum contagiosum, smallpox, human immunodeficiency virus (HIV), human papilloma virus (HPV), RS virus, norovirus, cytomegalovirus (CMV), varicella zoster virus (VZV), rhinovirus, adenovirus, coronavirus, influenza, and parainfluenza; bacterial diseases such as tuberculosis, Mycobacterium Avium, and Hansen's disease; infections such as mycosis, chlamydia, Candida, Aspergillus, cryptococcal meningitis, Pneumocystis carini, cryptosporidiosis, histoplasmosis, toxoplasmosis, malaria, Trypanosoma infection, and leishmaniasis. Examples of the active ingredient of the vaccine for preventing infectious include, but not limited to, substances derived from microorganisms/pathogens including bacteria, fungi, protozoa, and viruses which cause infectious diseases, such as antigenic protein, antigen peptide (partial peptide) from said antigenic protein, polysaccharide, lipid, and a combination thereof or a combination of the substance derived from said microorganisms/pathogen and a carrier.

Examples of the viral antigenic peptide derived from the viral antigen include, but are not limited to, influenza matrix protein peptide 58-66 (Jager E et al., Int. J. Cancer 67: 54 (1996)), HPV16 E7 peptide 86-93 (van Driel W J et al., Eur. J. Cancer 35:946 (1999)), HPV E7 peptide 12-20 (Scheibenbogen C et al., J. Immunother 23: 275 (2000)), HPV16 E7 peptide 11-20 (Smith J W I et al., J. Clin. Oncol. 21: 1562 (2003)), HSV2 gD (Berman P W et al., Science 227: 1490 (1985)), CMV gB (Frey S E et al., Infect Dis. 180: 1700 (1999), Gonczol E. et al., Exp. Opin. Biol. Ther. 1: 401 (2001)), and CMV pp 65 (Rosa C L et al., Blood 100: 3681 (2002), Gonczol E. et al., Exp. Opin. Biol. Ther. 1: 401 (2001)).

The carrier as used herein is a substance, such as protein and lipid, to which an antigenic protein or an antigenic peptide is bound chemically and/or physically, and examples include, but are not limited to, CRM 197 (Vaccine. 2013 Oct. 1; 31(42):4827-33), KLH (Cancer Immunol Immunother. 2003 October; 52(10):608-16), virus-like particles (PLoS ONE 5(3): e9809) and liposomes (J Liposome Res. 2004; 14(3-4):175-89).

The antigenic protein may be prepared by cloning cDNA, which encodes the antigenic protein, and expression in a host cell, according to a textbook such as Molecular Cloning 2nd ed., Cold Spring Harbor Laboratory Press (1989).

The synthesis of the antigenic peptide can be carried out according to a method generally used in peptide chemistry, for example, as described in literatures (Peptide Synthesis, Interscience, New York, 1966; The Proteins, Vol. 2, Academic Press Inc., New York, 1976).

The present invention further provides a kit comprising:
a) a liposome of the invention;
b) an antigen; and
c) a container or device to contain a unit dosage form of a) and b) in combination or separately.

The antigen is not limited so long as it is an antigen that may be used as an active ingredient of vaccines, and examples include antigenic proteins as mentioned above, antigenic peptides (partial peptides) derived from such antigenic proteins, and a complex thereof with a carrier.

In one embodiment of the present invention, there is provided a use of a liposome of the invention for the manufacture of a vaccine adjuvant.

In one embodiment of the present invention, there is provided a use of a liposome of the invention, as a vaccine adjuvant in the manufacture of a vaccine for the treatment of a disease or condition.

Also, in one embodiment of the present invention, there is provided a method for the treatment, prevention of or prevention of the progress of the diseases, comprising a step of administering a liposome of the invention, together with an antigen, to a patient.

The present invention will be further described with reference to the following examples which should not be regarded as limiting in any respect.

EXAMPLES

THF: tetrahydrofuran

EtOAc: ethyl acetate

NMP: N-methylpyrrolidinone

TEA: triethylamine

The measurement conditions for high performance liquid chromatography mass spectrometry (LCMS) were as follows. The observed MS (m/z) values were shown with respect to M+H.

MS detector: LCMS-IT-TOF

HPLC: Shimadzu Nexera X2 LC 30AD

Column: Kinetex 1.7μ C18 100A New column 50×2.1 mm

Flow rate: 1.2 ml/min

Measurement wavelength: 254 nm

Mobile phase: Solution A: 0.1% aqueous formic acid solution

Solution B: acetonitrile

Time program:

Step time (min)

1 0.01-1.40 Solution A: Solution B=90:10 to 5:95

2 1.40-1.60 Solution A: Solution B=5:95

3 1.61-2.00 Solution A: Solution B=99:1

Preparation of the Conjugated Compound

Preparation Example 1

(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide

[Chem. 22]

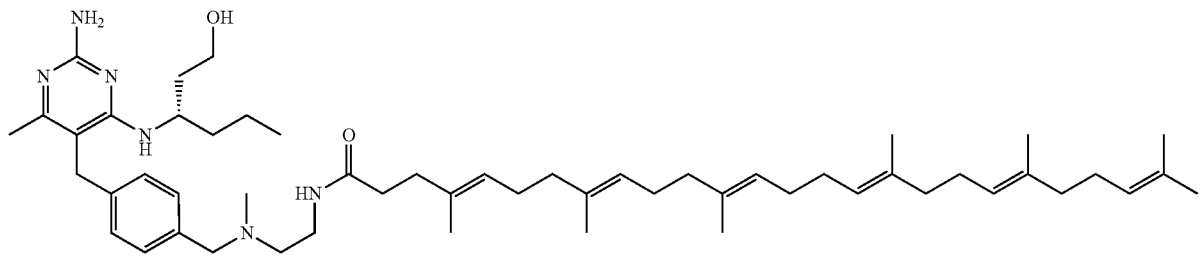

Step 1

[Chem. 23]

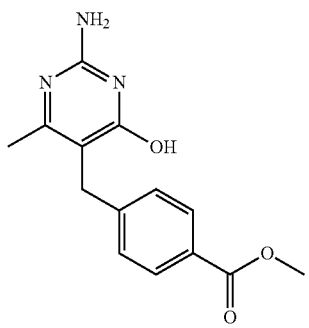

Methyl 4-(2-(ethoxycarbonyl)-3-oxobutyl)benzoate (3.56 g, 12.8 mmol) and guanidine carbonate (4.61 g, 25.6 mmol) were dissolved in methanol (23 ml), and the mixture was heated to reflux with stirring for 7 hour. After cooling the reaction mixture, water (30 ml) and acetic acid (0.660 ml, 11.5 mmol) were added. The precipitated solid was collected by filtration. The solid was suspended in THF and heated to reflux with stirring for one hour. After cooling, the solid was collected by filtration, washed with THF and dried to obtain the desired product (1.62 g, 46%).

$^1$H-NMR (400 MHz, DMSO-d$^6$) δ2.00 (3H, s), 3.71 (2H, s), 3.82 (3H, s), 6.35 (1H, br), 7.31 (2H, d, J=8.3 Hz), 7.84 (2H, d, J=8.3 Hz).

Step 2

[Chem. 24]

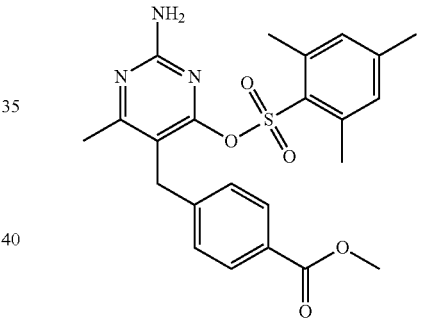

The compound obtained in Step 1 (1.62 g, 5.93 mmol) and N,N,N',N'-tetramethyl-1,3-propanediamine (1.41 ml, 8.89 mmol) were suspended in THF (24 ml), and 2-mesitylenesulfonyl chloride (1.94 g, 8.89 mmol) was added. The mixture was stirred at room temperature for 20 hours. Water was added to the mixture. The mixture was extracted with ethyl acetate. The organic layer was washed with brine, dried over anhydrous sodium sulfate, filtered, and concentrated under reduced pressure. The obtained solid was washed with ether, and with hexane, and dried to obtain the desired product (2.69 g, 99.6%).

$^1$H-NMR (400 MHz, DMSO-d$^6$) δ2.20 (3H, s), 2.29 (3H, s), 2.48 (6H, s), 3.84 (3H, s), 3.88 (2H, s), 6.35 (1H, br), 7.08 (2H, s), 7.19 (2H, d, J=8.3 Hz), 7.85 (2H, d, J=8.3 Hz).

Step 3

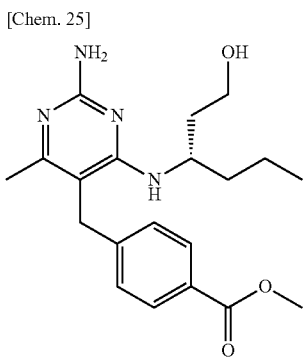

Methyl 4-((2-amino-4-((mesitylsulfonyl)oxy)-6-methylpyrimidin-5-yl)methyl)benzoate (3.6 g, 8.0 mmol) was dissolved in propionitrile (80 ml). (S)-(+)-3-amino-1-hexanol (5.6 g, 48 mmol) and trifluoroacetic acid (1.2 ml, 16 mmol) were added, and the mixture was heated to 110° C. After stirring for 36 hours, the mixture was cooled to room temperature and concentrated under reduced pressure. The residue was purified on silica gel column (ethyl acetate:methanol=20:1 to 5:1) to obtain the desired product (2.1 g, 71%).

$^1$H-NMR (CDCl$_3$) δ 0.73 (t, J=7.2 Hz, 3H), 0.90-1.76 (m, 6H), 2.41 (s, 3H), 3.49-3.61 (m, 2H), 3.69-3.87 (m, 2H), 3.90 (s, 3H), 4.24 (m, 1H), 7.17 (d, J=8.0 Hz, 2H), 7.98 (d, J=8.0 Hz, 2H).

Step 4

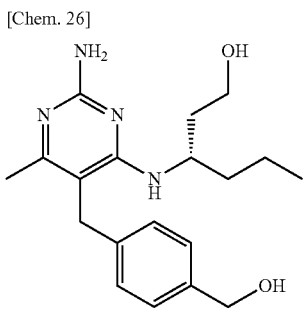

(S)-Methyl 4-((2-amino-4-((1-hydroxyhexan-3-yl)amino)-6-methylpyrimidin-5-yl)methyl)benzoate] (2.1 g, 5.6 mmol) was dissolved in tetrahydrofuran (56 mL)/methanol (5.6 mL). Lithium borohydride (3M in tetrahydrofuran, 5.6 mL, 17 mmol) was added, and the mixture was heated to 60° C. After stirring for 2 hours, lithium borohydride (3M in tetrahydrofuran, 5.6 mL, 17 mmol) was added, and the mixture was further stirred at 60° C. for 2 hours. After cooling to 0° C., 4N hydrochloric acid (30 mL) was added. The mixture was stirred at room temperature for 1 hour, neutralized with aqueous sodium hydrogen carbonate solution, and then extracted with ethyl acetate. The organic layer was washed with brine, dried over magnesium sulfate, and concentrated under reduced pressure to obtain a crude product (1.2 g).

$^1$H-NMR (CD$_3$OD) δ 0.78 (t, J=7.2 Hz, 3H), 1.03-1.76 (m, 6H), 2.18 (s, 3H), 3.41-3.48 (m, 2H), 3.76-3.88 (m, 2H), 4.23 (m, 1H), 4.55 (s, 2H), 7.11 (d, J=8.0 Hz, 2H), 7.26 (d, J=8.0 Hz, 2H).

Step 5

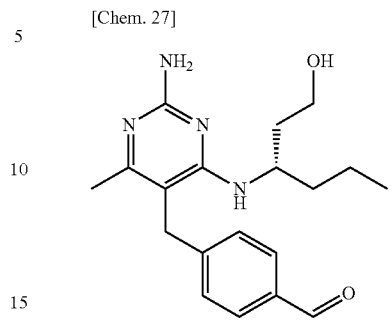

(S)-3-((2-Amino-5-(4-(hydroxymethyl)benzyl)-6-methylpyrimidin-4-yl)amino)hexan-1-ol (1.2 g, 3.5 mmol) was dissolved in chloroform (35 mL)/methanol (3.5 mL), and manganese dioxide (3.1 g, 35 mmol) was added. The mixture was stirred overnight and filtered through celite. The filtrate was concentrated under reduced pressure. The residue was purified on silica gel column (chloroform:methanol=99:1 to 4:1) to obtain the desired product (0.72 g, 37% in 2 Steps).

$^1$H-NMR (CD$_3$OD) δ 0.70 (t, J=7.2 Hz, 3H), 1.05-1.77 (m, 6H), 2.20 (s, 3H), 3.42-3.50 (m, 2H), 3.90-4.03 (m, 2H), 4.32 (m, 1H), 7.35 (d, J=8.0 Hz, 2H), 7.84 (d, J=8.0 Hz, 2H), 9.93 (s, 1H).

Step 6

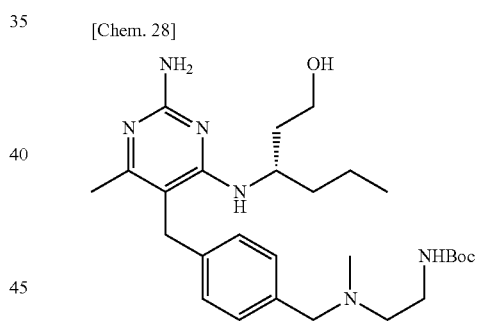

(S)-4-((2-Amino-4-((1-hydroxyhexan-3-yl)amino)-6-methylpyrimidin-5-yl)methyl)benzaldehyde (0.28 g, 0.82 mmol) was dissolved in chloroform (8 mL). t-Butyl (2-(methylamino)ethyl)carbamate (0.29 g, 1.6 mmol), acetic acid (0.23 mL, 4.1 mmol) and sodium triacetoxyborohydride (0.52 g, 2.5 mmol) were added. The mixture was stirred overnight at room temperature. Water was added, and the mixture was extracted with ethyl acetate. The organic layer was washed with brine, dried over magnesium sulfate, concentrated under reduced pressure. The residue was purified on amino silica gel column (ethyl acetate:methanol=99:1 to 95:5) to obtain a crude product (0.23 g, 56%).

$^1$H-NMR (CDCl$_3$) δ 0.66 (t, J=7.2 Hz, 3H), 0.91-1.77 (m, 6H), 1.40 (s, 9H), 2.12 (s, 3H), 2.26 (s, 3H), 2.39-2.44 (m, 2H), 3.15-3.46 (m, 4H), 3.43 (s, 2H), 3.61-3.86 (m, 2H), 4.05 (m, 1H), 4.67-4.77 (br, 2H), 4.91-5.01 (br, 1H), 7.05 (d, J=8.0 Hz, 2H), 7.18 (d, J=8.0 Hz, 2H).

Step 7

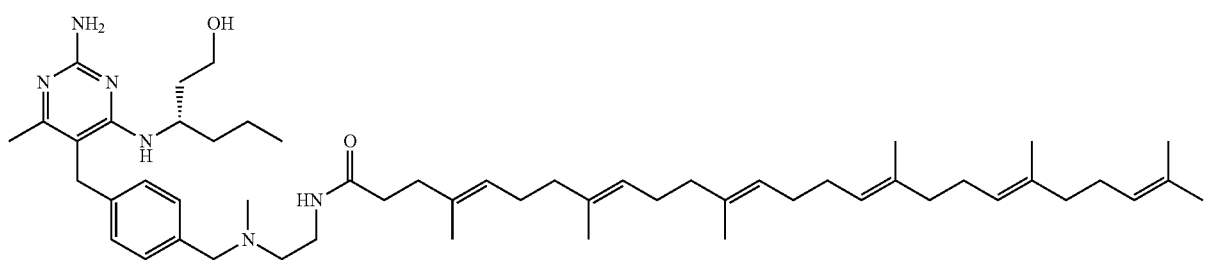

(S)-Butyl (2-((4-((2-amino-4-((1-hydroxyhexan-3-yl)amino)-6-methylpyrimidin-5-yl)methyl)benzyl)(methyl)amino)ethyl)carbamate (0.150 g, 0.29 mmol) was dissolved in chloroform (4 mL). Hydrogen chloride (4M in cyclopentyl methyl ether, 2.2 ml, 8.80 mmol) was added. The mixture was stirred at room temperature for hour and then concentrated under reduced pressure. (4E,8E,12E,16E,20E)-4,8,12,17,21,25-Hexamethylhexacosa-4,8,12,16,20,24-hexaenoic acid (123 mg, 0.262 mmol), 1-[bis(dimethylamino)methylene]-1H-1,2,3-triazolo[4,5-b]pyridin-1-ium 3-oxide hexafluorophosphate (150 mg, 0.393 mmol) and N,N-diisopropylethylamine (0.137 ml, 0.787 mmol) were dissolved in N,N-dimethyl formamide (3 ml), and the mixture was stirred for 5 min. The crude product was dissolved in N,N-dimethyl formamide (3 ml) and added to the mixture. The mixture was stirred overnight at room temperature. Water was added, and the mixture was extracted with ethyl acetate. The organic layer was washed with brine, dried over magnesium sulfate, and concentrated under reduced pressure. The residue was purified on amino silica gel column (chloroform:methanol=99:1 to 90:10) to obtain the desired product (80 mg, 32%).

$^1$H-NMR (CDCl$_3$) δ 0.71 (t, J=7.2 Hz, 3H), 0.92-1.83 (m, 27H), 1.95-2.08 (m, 20H), 2.18-2.32 (m, 10H), 2.46 (t, J=6.0 Hz, 2H), 3.28-3.43 (m, 4H), 3.46 (s, 2H), 3.64-3.81 (m, 2H), 4.10 (m, 1H), 4.48-4.58 (br, 2H), 5.06-5.17 (m, 6H), 5.94-6.04 (br, 1H), 7.06 (d, J=8.0 Hz, 2H), 7.20 (d, J=8.0 Hz, 2H). ESI: [M+H]$^+$ 852.6

Preparation Example 2

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one

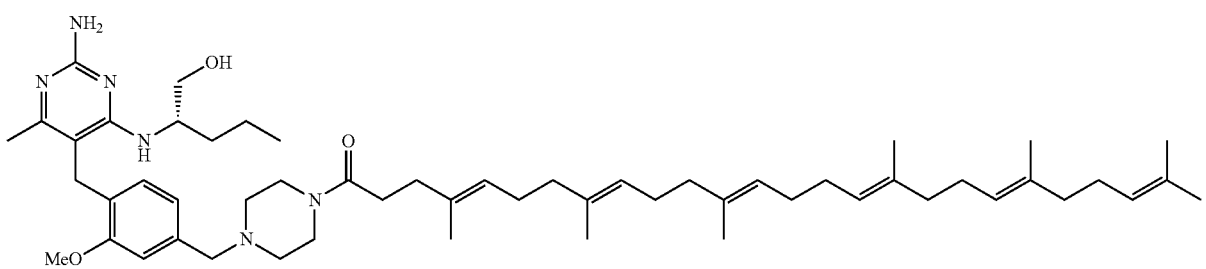

The desired product (96 mg, 23% in 2 Steps) was obtained in the similar manner as Step 6 and Step 7 of Preparation Example 1, using known compound (S)-4-((2-amino-4-((1-hydroxypentan-2-yl)amino)-6-methylpyrimidin-5-yl)methyl)-3-methoxybenzaldehyde (0.10 g, 0.28 mmol), t-butyl piperazin-1-carboxylate (0.13 g, 0.71 mmol) and (4E,8E,12E,16E,20E)-4,8,12,17,21,25-hexamethylhexacosa-4,8,12,16,20,24-hexaenoic acid (72 mg, 0.15 mmol).

$^1$H-NMR (CDCl$_3$) δ 0.77 (t, J=7.2 Hz, 3H), 1.00-1.44 (m, 4H), 1.57-1.65 (m, 21H), 1.88-2.04 (m, 20H), 2.23-2.38 (m, 11H), 3.38-3.74 (m, 6H), 3.44 (s, 2H), 3.67 (s, 2H), 3.88 (s, 3H), 4.00 (m, 1H), 4.77-4.87 (br, 2H), 5.03-5.11 (m, 6H), 6.79 (d, J=8.0 Hz, 1H), 6.86 (s, 1H), 6.89 (d, J=8.0 Hz, 1H). ESI: [M+H]$^+$ 879.6

Preparation Example 3

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one

[Chem. 31]

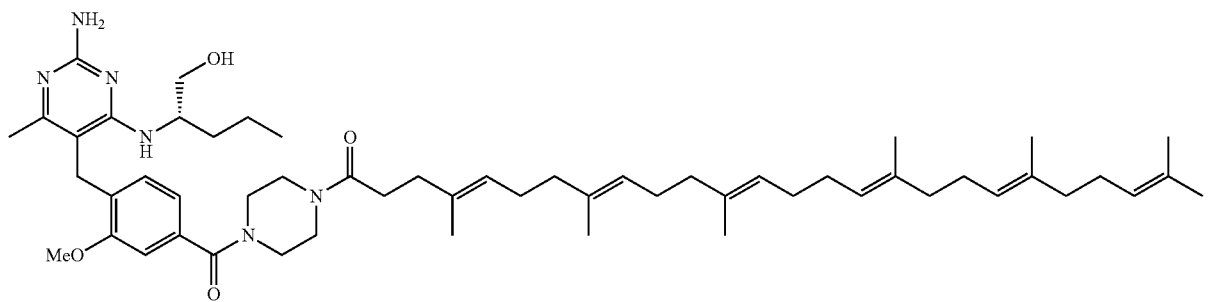

Step 1

[Chem. 32]

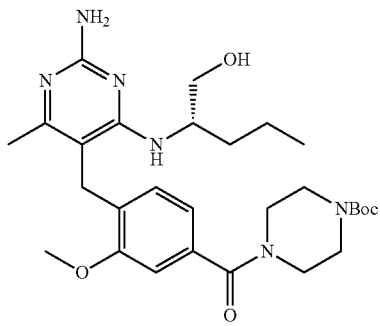

(S)-4-((2-Amino-4-((1-hydroxypentan-2-yl)amino)-6-methylpyrimidin-5-yl)methyl)-3-methoxybenzoic acid (190 mg, 0.507 mmol), which was prepared as described in WO2012/066336, and 1-BOC-piperazine (142 mg, 0.761 mmol) were dissolved in N,N-diethylformamide (5 ml). 1-[Bis(dimethylamino)methylene]-1H-1,2,3-triazolo[4,5-b]pyridinium 3-oxide hexafluorophosphate (289 mg, 0.761 mmol) and N,N-diisopropylethylamine (197 mg, 1.52 mmol) were added, and the mixture was stirred at room temperature for 10 hours. Water was added to the mixture, and the mixture was extracted with chloroform. The organic layer was dried over anhydrous sodium sulfate, filtered, and concentrated under reduced pressure. The resulting residue was purified on silica gel column chromatography (ethyl acetate/methanol=20/1 to 5/1) to obtain the desired product (202 mg, 73%) as colorless amorphous.

MS (ESI+): [M+H]$^+$ 543.4

Step 2

[Chem. 33]

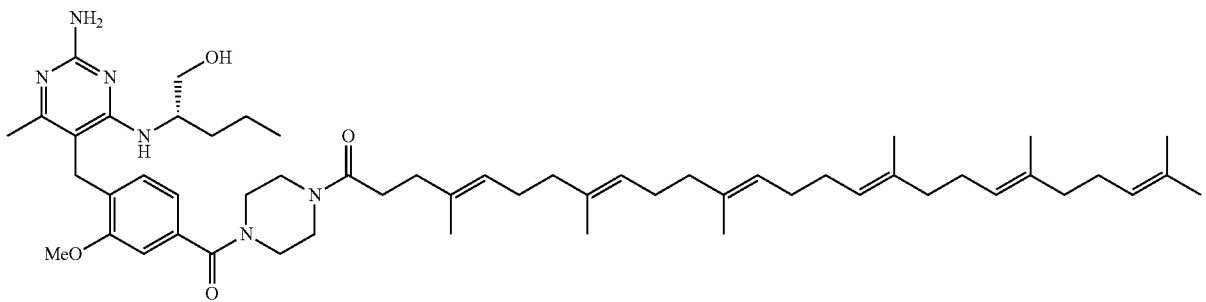

(S)-tert-Butyl 4-(4-((2-amino-4-((1-hydroxypentan-2-yl)amino)-6-methylpyrimidin-5-yl)methyl)-3-methoxybenzoyl)piperazin-1-carboxylate (200 mg, 0.369 mmol) was dissolved in chloroform (3.0 ml). 4M Hydrochloric acid-cyclopentyl methyl ether solution (3 ml, 12.0 mmol) was added, and the mixture was stirred at room temperature for 1 hour. Toluene was added to the reaction mixture, and the mixture was concentrated under reduced pressure. The residue was added to the solution of (4E,8E,12E,16E,20E)-4,8,12,17,21,25-hexamethylhexacosa-4,8,12,16,20,24-hexaenoic acid (166 mg, 0.355 mmol), [bis(dimethylamino)methylene]-1H-1,2,3-triazolo[4,5-b]pyridinium 3-oxide hexafluorophosphate (202 mg, 0.532 mmol) and N,N-diisopropyl ethyl amine (0.185 ml, 1.065 mmol) in N,N-dimethyl formamide (5 ml), and the mixture was stirred at room temperature for 6 hours. Water was added to the mixture, and the mixture was extracted with chloroform. The organic layer was washed with brine, dried over anhydrous sodium sulfate, filtered, and concentrated under reduced pressure. The residue was purified on silica gel column chromatography (chloroform/methanol 20/1) to obtain the title compound (159 mg, 50%).

$^1$H-NMR (CDCl$_3$) δ 0.83 (t, J=7.3 Hz, 3H), 1.15-1.48 (m, 4H), 1.58-1.68 (m, 21H), 1.94-2.15 (m, 20H), 2.25-2.32 (m, 2H), 2.32 (s, 3H), 2.40-2.48 (m, 2H), 3.37-3.80 (m, 12H), 3.93 (s, 3H), 3.99-4.05 (m, 1H), 4.65 (brs, 2H), 4.80 (br, 1H), 5.07-5.18 (m, 6H), 6.86 (dd, J=7.8, 1.4 Hz, 1H), 6.97-7.00 (m, 2H). MS (ESI+): [M+H]$^+$ 893.6

Preparation Example 4

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide Step 1

[Chem. 35]

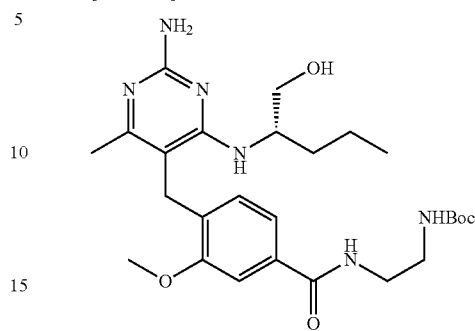

The title compound (216 mg, 78%) was obtained, in the similar manner as Step 1 of Preparation Example 3, using (S)-4-((2-amino-4-((1-hydroxypentan-2-yl)amino)-6-methylpyrimidin-5-yl)methyl)-3-methoxybenzoic acid (0.14 g, 0.41 mmol), which was prepared as described in WO2012/066336, and tert-butyl (2-aminoethyl)carbamate (137 mg, 0.855 mmol).

$^1$H-NMR (CDCl$_3$) δ 0.81 (t, J=7.3 Hz, 3H), 1.07-1.40 (m, 4H), 1.47 (s, 9H), 2.32 (s, 3H), 3.37-3.45 (m, 3H), 3.52-3.57 (m, 2H), 3.63-3.67 (m, 1H), 3.74 (s, 2H), 3.97 (s, 3H), 3.97-4.03 (m, 1H), 4.58 (br, 2H), 4.75-4.77 (br, 1H), 4.97-4.99 (br, 1H), 6.95-6.98 (m, 1H), 7.22-7.23 (m, 1H), 7.27-7.31 (br, 1H), 7.47-7.49 (m, 1H).

[Chem. 34]

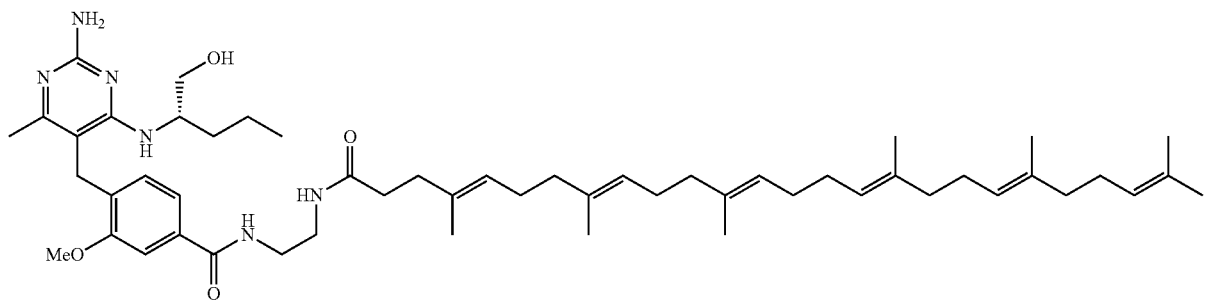

Step 2

[Chem. 36]

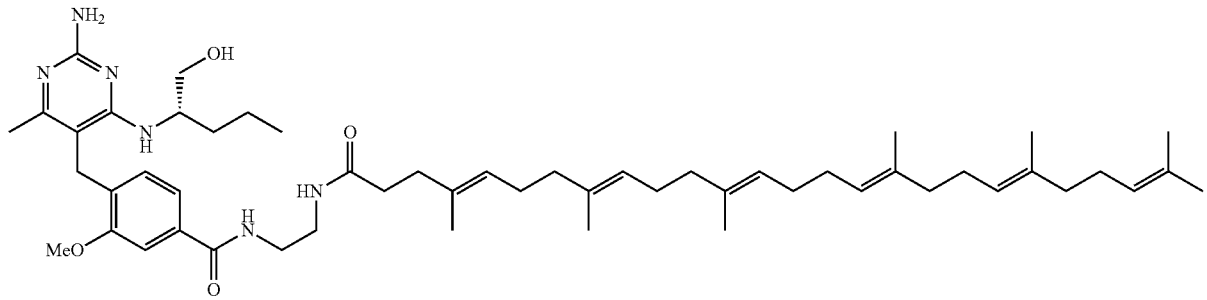

The title compound (84.0 mg, 24%) was obtained, in the similar manner as Step 2 of Preparation Example 3, using the compound obtained in Step 1 (205 mg, 0.397 mmol).

$^1$H-NMR (CDCl$_3$) δ 0.81 (t, J=7.3 Hz, 3H), 1.07-1.46 (m, 4H), 1.55-1.70 (m, 21H), 1.90-2.10 (m, 20H), 2.26-2.30 (m, 4H), 2.33 (s, 3H), 3.38-3.44 (m, 1H), 3.46-3.58 (m, 4H), 3.62-3.67 (m, 1H), 3.74 (s, 2H), 3.97 (s, 3H), 3.97-4.03 (m, 1H), 4.54-4.57 (br, 2H), 4.76-4.79 (br, 1H), 5.06-5.15 (m, 6H), 6.10-6.14 (br, 1H), 7.00 (d, J=8.0 Hz, 1H), 7.24 (dd, J=8.0, 1.6 Hz, 1H), 7.38-7.41 (br, 1H), 7.45 (d, J=1.6 Hz, 1H). MS (ESI+): [M+H]$^+$ 867.6.

Preparation Example 5

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide

[Chem. 37]

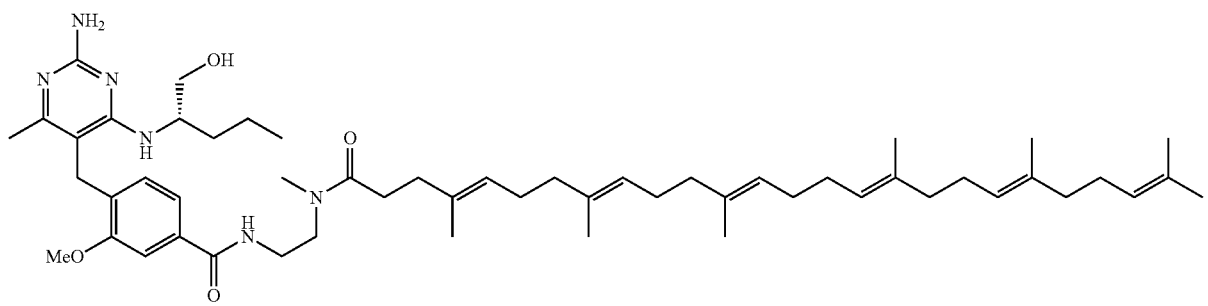

Step 1

[Chem. 38]

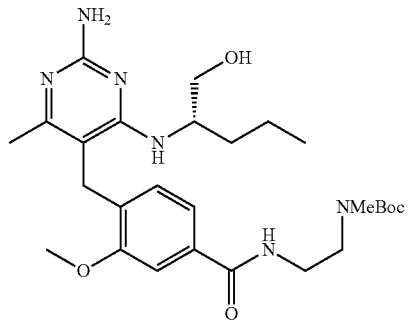

The title compound (242 mg, 81%) was obtained, in the similar manner as Step 1 of Preparation Example 3, using (S)-4-((2-amino-4-((1-hydroxypentan-2-yl)amino)-6-methylpyrimidin-5-yl)methyl)-3-methoxybenzoic acid (0.14 g, 0.41 mmol), which was prepared as described in WO2012/

066336, and N-(2-aminoethyl)-N-methyl carbamic acid t-butyl ester (98 mg, 0.561 mmol).

$^1$H-NMR (CDCl$_3$) δ 0.84 (t, J=7.3 Hz, 3H), 1.07-1.41 (m, 4H), 1.43 (s, 9H), 2.31 (s, 3H), 2.91 (s, 3H), 3.39-3.44 (m, 1H), 3.45-3.55 (m, 2H), 3.56-3.61 (m, 2H), 3.62-3.67 (m, 1H), 3.73 (s, 2H), 3.96 (s, 3H), 3.97-4.02 (m, 1H), 4.55-4.59 (br, 2H), 4.74-4.78 (br, 1H), 6.94-6.97 (m, 1H), 7.21-7.24 (m, 1H), 7.47-7.50 (m, 2H).

Step 2

[Chem. 39]

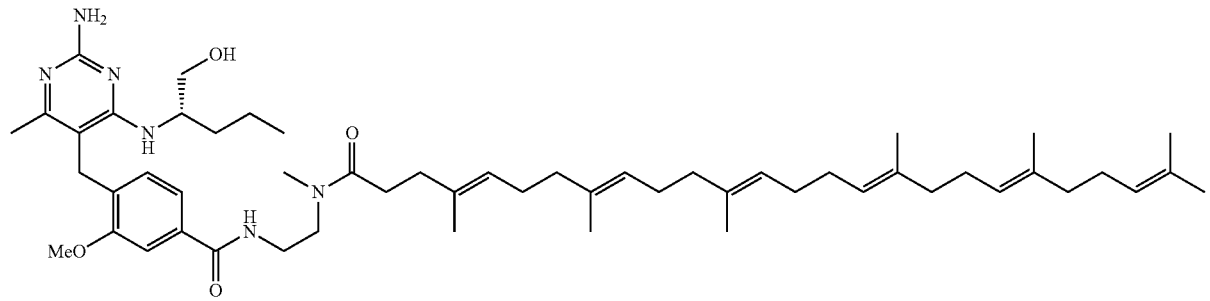

The title compound (149 mg, 38%) was obtained, in the similar manner as Step 2 of Preparation Example 3, using the compound obtained in Step 1 (236 mg, 0.445 mmol).

$^1$H-NMR (CDCl$_3$) δ 0.80 (t, J=7.3 Hz, 3H), 1.06-1.45 (m, 4H), 1.56-1.68 (m, 21H), 1.90-2.09 (m, 20H), 2.21-2.31 (m, 2H), 2.33 (s, 3H), 2,37-2.43 (m, 2H), 3.08 (s, 3H), 3.37-3.45 (m, 1H), 3.55-3.69 (m, 5H), 3.73 (s, 2H), 3.96 (s, 3H), 3.97-4.03 (m, 1H), 4.55-4.58 (br, 2H), 4.77-4.80 (br, 1H), 5.06-5.14 (m, 6H), 7.00 (d, J=8.0 Hz, 1H), 7.24 (dd, J=8.0, 1.2 Hz, 1H), 7.44 (d, J=1.6 Hz, 1H), 7.53-7.55 (br, 1H). MS (ESI+): [M+H]$^+$ 881.6

Preparation of Liposome

The solutions containing the lipid components and the compound of Preparation Example 1 as shown in Table 1 in chloroform were prepared. Each solution was put in an eggplant flask and stirred for 30 minutes at 37° C. Under nitrogen atmosphere, the solvent was removed at 37° C. and dried in vacuo. The residue was added with PBS and rehydrated. The thin film was detached using batch-type ultrasonication, and then, stirred at 37° C. for 1 hour. The liposomes were obtained after extrusion (room temperature, 400 nm) and sterilized through 0.22 μm filter.

TABLE 1

| Example | Lipid components of liposome (molar ratio) | Compound/Lipid (weight ratio) |
|---|---|---|
| 1 | HSPC/Chol/DSPG (53.1/26.3/20.5) | 1/10 |
| 2 | HSPC/Chol/DSPG (53.1/26.3/20.5) | 1/2 |
| 3 | DOPC/Chol/DOPG (53.1/26.3/20.5) | 1/10 |
| 4 | DOPC/Chol/DOPC (53.1/26.3/20.5) | 1/2 |
| 5 | DMPC/EPG (62.5/37.5) | 1/10 |
| 6 | DMPC/EPG (62.5/37.5) | 1/2 |

HSPC: Hydrogenated soybean phosphatidylcholine (Nippon Yushi; COATSOME NC-21E)
DOPC: Dioleoylphosphatidylcholine (Nippon Yushi; COATSOME MC-8181)
DSPG: Distearoylphosphatidylglycerol, sodium salt (Nippon Yushi; COATSOME MG-80801S)
DOPG: Dioleoylphosphatidylglycerol, sodium salt (Nippon Yushi; COATSOME MG-8181LS)
DMPC: Dimyristoylphosphatidylcholine (Nippon Yushi; COATSOME MC-4040)
EPG: Egg yolk phosphatidylglycerol (Nippon Yushi; COATSOME NG-50LS)
Chol: cholesterol (Nippon Yushi; Cholesterol (HP))

Test Example 1

The appearance of the liposomes of the Examples was visually observed. Creaming was observed in the liposome of Example 3, and precipitation was observed in the liposomes of Example 4 and Example 6. The liposomes of the Examples immediately after the preparation were diluted 5-fold with purified water, and the particle size distribution and the surface charge were measured by dynamic light scattering using MALVERN Zetasizer Nano (see Table 2). The particle size distribution and the Zeta potential distribution of the liposome of Example 5 are shown in FIG. 1. The liposomes of Example 1 and Example 5, which polydispersity index was relatively small, were left to stand for 6 weeks in a refrigerator (4° C.) and diluted 5-fold with purified water, followed by measurements for particle size distribution and surface charge by dynamic light scattering using MALVERN Zetasizer Nano. The particle size distribution and the surface charge were confirmed as being almost equivalent to those of the liposome immediately after the preparation. For each Example, the content of the conjugated compound in the liposome was determined by an external standard method. That is, the content was determined using a calibration curve, which was prepared based on the absorbances at the maximum absorption wavelength of 288 nm of the standard sample.

TABLE 2

| Example | Average particle size (nm) | Polydispersity index (PDI) | Surface charge (Z-potential, mV) | Conjugated compound concentration (mg/mL) |
|---|---|---|---|---|
| 1 | 148.4 | 0.194 | −67.8 | 0.235 |
| 2 | 178.7 | 0.327 | −65.5 | 0.324 |
| 3 | 241.7 | 0.243 | −36.1 | 1.000 |
| 4 | 340.2 | 0.463 | 9.24 | 1.850 |
| 5 | 166.3 | 0.206 | −66.9 | 0.365 |
| 6 | 172.0 | 0.245 | −27.9 | 2.307 |

From the above results, it is shown that the liposomes of Example 1 and Example 5 have high monodispersity and high stability.

In the following test examples, the liposomes of Example and Example 5 were used within six weeks after the preparation thereof.

Test Example 2

For the first immunization, a mixed solution (100 μL/mouse) of equal volume of ovalbumin (OVA) (2 mg/mL)

and the compound of Preparation Example 1 (0.008 to 1 mg/mL) was administered intramuscularly to gastrocnemius muscle of C57BL/6 male mice (7 or 8 week-old). Two weeks later, an equal amount of the same mixture was administered intramuscularly to the gastrocnemius muscle for booster immunization. One week after the booster immunization, cardiac blood was collected under isoflurane inhalation anesthesia, and serum was collected by centrifugation. The OVA-specific IgG2c values in the serum were determined by ELISA method. Specifically, OVA solution (SIGMA) was added to a 96-well plate, followed by blocking with 1% skim milk (Wako Pure Chemical Industries, Ltd.), and the serum sample diluted with phosphate buffer was added and then a secondary antibody (goat anti-mouse IgG1 (Jackson) or IgG2c (Southern Bio)) was added. SureBlue™ TMB microwell peroxidase substrate (KPL) was added, and the product of the enzyme reaction was measured by microplate reader (See FIG. 2).

The liposomes of Example 1 and Example 5 induced OVA-specific IgG2c, which was significantly enhanced as compared to the negative control group. In particular, the liposome of Example 5 induced significantly enhanced OVA-specific IgG2c production, as compared to the negative control group.

Test Example 3

The spleen cells were prepared from the mouse of Test Example 2. The cells were added with OVA and Brefeldin A (eBioscience) and cultured overnight. The cultured cells were harvested, stained with APC-labeled anti-mouse CD3e antibody, FITC-labeled anti-mouse CD4 antibody and Fixable Viability Dye Fluor® 450 (eBioscience), and fixed in Fixation/Permeabilization buffer (eBioscience). After treatment in Permeabilization buffer (eBioscience), the cells were stained with antibody cocktail PerCP-Cy5.5-labeled anti-IFN-γ antibody, PE-Cy7-labeled anti-IL-2 antibody, and PE-labeled TNF-α (eBioscience). Data acquisition and analysis were performed using FACS Cant II (BD Biosciences) and FLOWJO software (TreeStar). The results were shown in FIG. 3.

The spleen cells were also stained with eFluor 450-labeled anti-mouse CD3e antibody, Alexa Fluor® 647-labeled anti-mouse CD8 antibody, PE-labeled H-2K$^b$ OVA Tetramer-SINFEKL (MBL) and Flexable Viability Dye eFluor 520 (eBioscience). Data acquisition and analysis were performed using FACS Cant II (BD Biosciences) and FLOWJO software (TreeStar). The results are shown in FIG. 4.

The spleen cells were further incubated with antibody cocktail eFluor450-labeled anti-mouse CD3e antibody, Alexa Fluor647-labeled anti-mouse CD8 antibody, PE-Cy7-labeled anti-mouse CD44 antibody, PerCP-Cy5.5-labeled anti-mouse CD62L antibody and Fixable Viability Dye520 (eBioscience). Data acquisition and analysis were performed using FACS Cant II (BD Biosciences) and FLOWJO software (TreeStar). The results were shown in FIG. 5.

The liposome of Example 1 and Example 5 significantly increased the proportion of OVA-specific type 1 helper T cells, particularly OVA-specific multifunctional CD4-positive T lymphocytes, the proportion of MHC-restricted OVA-specific CD8-positive T lymphocytes (OVA tetramer CD8-positive T cells in FIG. 3), and the proportion of CD8-positive effector memory T lymphocytes, as compared to the negative control group. In particular, the liposome of Example 5 significantly increased the proportion of OVA-specific multifunctional CD4 positive T lymphocytes and the proportion of MHC-restricted OVA-specific CD8-positive T lymphocytes as compared to the negative control group.

INDUSTRIAL APPLICABILITY

The liposome of the present invention is useful as an adjuvant, which is added to a vaccine preparation, for enhancement of the immunostimulating effect.

The invention claimed is:

1. A liposome comprising (1) and (2):
   (1) a lipid multilayer comprising a mixture of two different lipids selected from the group consisting of: hydrogenated soybean phosphatidylcholine (HSPC), dioleoylphosphatidylcholine (DOPC), distearoylphosphatidylglycerol (DSPG), dioleoylphosphatidylglycerol (DOPG), dimyristoylphosphatidylcholine (DMPC) and egg yolk phosphatidylglycerol (EPG), or a mixture of the two different lipids and cholesterol (Chol); and
   (2) a conjugated compound encapsulated in the lipid multilayer of (1), wherein the conjugated compound is a compound of formula (1):

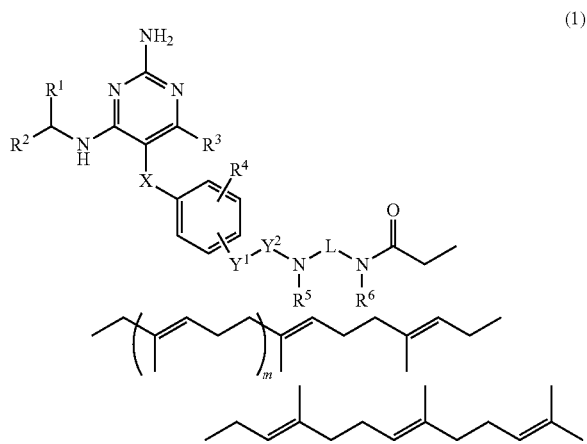

or a pharmaceutically acceptable salt thereof, wherein
   X is —CH$_2$—;
   R$^1$ and R$^2$ are independently H or C$_{1-6}$ alkyl, wherein the C$_{1-6}$ alkyl is optionally substituted with 1, 2, 3 or 4 substituents independently selected from the group consisting of hydroxy, halogen and C$_{1-6}$ alkoxy;
   R$^3$ is C$_{1-6}$ alkyl, C$_{1-6}$ alkoxy or C$_{1-6}$ alkylthio;
   R$^4$ is H, halogen, hydroxy, C$_{1-6}$ alkyl, C$_{1-6}$ alkoxy or cyano;
   Y$^1$ is a single bond or —(CR$^9$R$^{10}$)$_p$—;
   Y$^2$ is a single bond or —C(O)—;
   L is a straight chain C$_{2-6}$ alkylene, wherein the C$_{2-6}$ alkylene is optionally substituted with 1, 2, 3 or 4 substituents independently selected from the group consisting of C$_{1-5}$alkyl, hydroxy, and halogen;
   R$^5$ and R$^6$ are independently H or C$_{1-6}$ alkyl, wherein the C$_{1-6}$ alkyl is optionally substituted with 1, 2, 3 or 4 substituents independently selected from the group consisting of hydroxy and halogen;
   or R$^5$ and R$^6$ are taken together with -N-L-N-, to form piperazin-1,4-diyl, wherein the piperazin-1,4-diyl is optionally substituted with 1, 2, 3 or 4 substituents independently selected from the group consisting of methyl, ethyl, propyl, hydroxymethyl, hydroxyethyl, oxo, hydroxy and halogen;

$R^9$ and $R^{10}$ are independently selected from H and $C_{1-4}$ alkyl;

m is 1; and p is 1.

2. The liposome according to claim 1, wherein the weight ratio of the conjugated compound to the lipid components is 1:8 to 1:250.

3. The liposome comprising a conjugated compound according to claim 1, wherein the lipid multilayer of (1) is a lipid multilayer comprising lipid components comprising a mixture of dimyristoylphosphatidylcholine (DMPC) and egg yolk phosphatidylglycerol (EPG).

4. The liposome according to claim 1, wherein the molar ratio of dimyristoylphosphatidylcholine (DMPC) to egg yolk phosphatidylglycerol (EPG) is 1:1 to 2:1.

5. The liposome according to claim 1, wherein the lipid multilayer is a lipid bilayer.

6. A pharmaceutical composition comprising the liposome according to claim 1.

7. A vaccine adjuvant comprising the liposome according to claim 1.

8. A vaccine comprising the liposome according to claim 1, and an antigen.

9. The vaccine according to claim 8, wherein the antigen is a substance derived from a pathogen.

10. The liposome according to claim 1, wherein the conjugated compound is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;

(4E,8E,12E,16E,20E)-1-(4-{4-[(2-amino-4-{[(2S)-1-hydroxypentan-2-yl]amino}-6-methylpyrimidin-5-yl)methyl]-3- methoxybenzyl}piperazin-1-yl)-4,8,12,17,21,25-hexamethylhexacosa-4,8,12,16,20,24-hexaen-1-one;

(4E,8E,12E,16E,20E)-1-(4-{4-[(2-amino-4-{[(2S)-1-hydroxypentan-2-yl]amino}-6-methylpyrimidin-5-yl)methyl]-3- methoxybenzoyl}piperazin-1-yl)-4,8,12,17,21,25-hexamethylhexacosa-4,8,12,16,20,24-hexaen-hexamethylhexacosa-4,8,12,16,20,24-hexaen-1-one;

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; or 4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide.

11. The liposome according to claim 1, wherein the conjugated compound is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide.

12. The liposome according to claim 1, wherein:

the lipid multilayer of (1) comprises a mixture of dimyristoylphosphatidylcholine (DMPC) and egg yolk phosphatidylglycerol (EPG); and the conjugated compound of (2) being encapsulated in the lipid multilayer of (1) is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;

(4E,8E,12E,16E,20E)-1-(4-{4-[(2-amino-4-{[(2S)-1-hydroxypentan-2-yl]amino}-6-methylpyrimidin-5-yl)methyl]-3- methoxybenzyl}piperazin-1-yl)-4,8,12,17,21,25-hexamethylhexacosa-4,8,12,16,20,24-hexaen-1-one;

(4E,8E,12E,16E,20E)-1-(4-{4-[(2-amino-4-{[(2S)-1-hydroxypentan-2-yl]amino}-6-methylpyrimidin-5-yl)methyl]-3- methoxybenzoyl}piperazin-1-yl)-4,8,12,17,21,25-hexamethylhexacosa-4,8,12,16,20,24-hexaen-hexamethylhexacosa-4,8,12,16,20,24-hexaen-1-one;

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; or 4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide.

13. The liposome according to claim 1, wherein:

the lipid multilayer of (1) comprises a mixture of dimyristoylphosphatidylcholine (DMPC) and egg yolk phosphatidylglycerol (EPG); and the conjugated compound of (2) being encapsulated in the lipid multilayer of (1) is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide.

14. A kit comprising:

a) a liposome according to claim 1; and b) an antigen.

15. The liposome according to claim 1, wherein:

$Y^1$ is a —$(CR^9R^{10})_p$— and p is 1;

$Y^2$ is a single bond;

$R^1$ is $C_{1-6}$ alkyl;

$R^2$ is $C_{1-6}$ alkyl substituted with 1, 2, 3, or 4 hydroxy;

$R^3$ is $C_{1-6}$ alkyl;

$R^4$, $R^6$, $R^9$, and $R^{10}$ are each hydrogen;

$R^5$ is $C_{1-6}$ alkyl;

L is a straight chain $C_{2-6}$ alkylene;

m is 1; and p is 1.

* * * * *